(12) United States Patent
Pulici et al.

(10) Patent No.: US 8,791,265 B2
(45) Date of Patent: Jul. 29, 2014

(54) SULFONAMIDO DERIVATIVES OF 3,4-DIARYLPYRAZOLES AS PROTEIN KINASE INHIBITORS

(75) Inventors: Maurizio Pulici, Milan (IT); Chiara Marchionni, Milan (IT); Gabriella Traquandi, Milan (IT)

(73) Assignee: Nerviano Medical Sciences S.R.L., Nerviano (MI) (IT)

( * ) Notice: Subject to any disclaimer, the term of this patent is extended or adjusted under 35 U.S.C. 154(b) by 0 days.

(21) Appl. No.: 13/574,168

(22) PCT Filed: Jan. 19, 2011

(86) PCT No.: PCT/EP2011/050654
§ 371 (c)(1),
(2), (4) Date: Oct. 29, 2012

(87) PCT Pub. No.: WO2011/092088
PCT Pub. Date: Aug. 4, 2011

(65) Prior Publication Data
US 2013/0053419 A1 Feb. 28, 2013

(30) Foreign Application Priority Data
Jan. 27, 2010 (EP) .................................... 10151805

(51) Int. Cl.
*C07D 401/00* (2006.01)
*A61K 31/44* (2006.01)
*A61K 31/4439* (2006.01)
*C07D 401/04* (2006.01)

(52) U.S. Cl.
CPC ................................ *C07D 401/04* (2013.01); *A61K 31/4439* (2013.01)
USPC ........................................ 546/268.4; 514/341

(58) Field of Classification Search
None
See application file for complete search history.

(56) References Cited

FOREIGN PATENT DOCUMENTS

| WO | WO 98/52940 | 11/1998 |
| WO | WO 00/31063 | 6/2000 |
| WO | WO 03/055860 A1 | 7/2003 |
| WO | WO 2007/024843 A2 | 3/2007 |
| WO | WO 2007/105058 A2 | 9/2007 |
| WO | WO 2010/010154 A1 | 1/2010 |

OTHER PUBLICATIONS

International Search Report dated Jun. 4, 2011 for co-pending International Patent Application No. PCT/EP2011/050654.
Cohen, P. "The Development and Therapeutic Potential of Protein Kinase Inhibitors," *Current Opinion in Chemical Biology*, 1999, 3, 459-465.
Cohen, Y.; Xing, M.; Mambo, E.; Guo, Z.; Wu, G.; Trink, B.; Beller, U.; Westra, W.H.; Ladenson, P.W.; Sidransky, D. "BRAF Mutation in Papillary Thyroid Carcinoma," *J. Nat'l. Cancer Inst.*, 2003, 95, 625-627.
Davies, H.; Bignell, G.R.; Cox, C.; Stephens, P.; Edkins, S.; Clegg, S.; Teague, J.; Woffendin, H.; Garnett, M.J.; Bottomley, W.; Davis, N.; Dicks, E.; Ewing, R.; Floyd, Y.; Gray, K.; Hall, S.; Hawes, R.; Hughes, J.; Kosmidou V.; Menzies, A.; Mould, C.; Parker, A.; Stevens, C.; Watt, S.; Hooper, S.; Wilson, R.; Jayatilake, H.; Gusterson, B.A.; Cooper, C.; Shipley, J.; Hargrave, D.; Pritchard-Jones, K.; Maitland, N.; Chenevix-Trench, G.; Riggins, G.J.; Bigner, D.D.; Palmieri, G.; Cossu, A.; Flangan, A.; Nicholson, A.; Ho, J.W.C.; Leung, S.Y.; Yuen S.T.; Weber, B.L.; Seigler, H.F.; Darrow, T.L.; Paterson, H.; Marais, R.; Marshall, C.J.; Wooster, R.; Stratton, M.R.; Futreal, P.A. "Mutations of the BRAF Gene in Human Cancer," *Nature*, 2002, 417, 949-954.
Hagemann, C.; Rapp, U.R. "Isotype-Specific Functions of Raf Kinases," *Expt. Cell Res.*, 1999, 253, 34-46.
Hingorani, S.R.; Jacobetz, M.A.; Robertson, G.P.; Herlyn, M.; Tuveson, D.A. "Suppression of BRAF$^{V599E}$ in Human Melanoma Abrogates Transformation," *Cancer Res.*, 2003, 63, 5198-5202.
Hoshino, R.; Chatani, Y.; Yamori, T.; Tsuruo, T.; Oka, H.; Yoshida, O.; Shimada, Y.; Ari-i, S.; Wada, H.; Fujimoto, J.; Kohno, M. "Constitutive Activation of the 41-/43-kDa Mitogen-Activated Protein Kinase Signaling Pathway in Human Tumors," *Oncogene*, 1999, 18, 813-822.
Kolch, W.; Kotwaliwale, A.; Vass, K.; Janosch, P. "The Role of Raf Kinases in Malignant Transformation," *Exp. Rev. Mol. Med.*, 2002, 4, 1-18.
Mercer, K.E.; Pritchard, C.A. "RAF Proteins and Cancer: B-Raf is Identified as a Mutational Target," *Biochim. Biophys. Acta*, 2003, 1653, 25-40.
Peyssonnaux, C.; Eychene, A. "The Raf/MEK/ERK Pathway: New Concepts of Activation," *Biology of the Cell*, 2001, 93, 53-62.
Raju, U; Ariga, H.; Dittmann, K.; Nakata, E.; Ang, K.K.; Milas, L. "Inhibition of DNA Repair as a Mechanism of Enhanced Radioresponse of Head and Neck Carcinoma Cells by a Selective Cyclooxygenase-2 Inhibitor, Celecoxib," *Int. J. Radiation Oncology Biol. Phys.*, 2005, 63, 520-528.
Tannapfel, A.; Sommerer, F.; Benicke, M.; Katalinic, A.; Uhlmann, D.; Witzigmann, H.; Hauss, J.; Wittekind, C. *Gut*, 2003, 52, 706-712.
Velculescu, V.E. "Defining the Blueprint of the Cancer Genome," *Carcinogenesis*, 2008, 29, 1087-1091.
Wellbrock, C.; Ogilvie, L.; Hedley, D; Karasarides, M.; Martin, J.; Niculescu-Duvaz, D.; Springer, C.J.; Marais, R. "$^{V599E}$B-RAF is an Oncogene in Melanocytes," *Cancer Res.*, 2004, 64, 2338-2342.
Wojnowski, L.; Zimmer, A.M.; Beck, T.W.; Hahn, H.; Bernal, R.; Rapp, U.R.; Zimmer, A. "Endothelial Apoptosis in Braf-Deficient Mice," *Nature Genet.*, 1997, 16, 293-297.

*Primary Examiner* — Heidi Reese
(74) *Attorney, Agent, or Firm* — Brinks Gilson & Lione

(57) ABSTRACT

Compounds which are sulfonamido 3,4-diarylpyrazole derivatives, or pharmaceutically acceptable salts thereof, their preparation process and pharmaceutical compositions comprising them are disclosed; these compounds are useful in the treatment of diseases caused by and/or associated with an altered protein kinase activity such as cancer, viral infection, prevention of AIDS development in HIV-infected individuals, cell proliferative disorders, autoimmune and neurodegenerative disorders; also disclosed is their use as prodrugs.

22 Claims, 2 Drawing Sheets

SULFONAMIDO DERIVATIVES OF 3,4-DIARYLPYRAZOLES AS PROTEIN KINASE INHIBITORS

RELATED APPLICATIONS

This application is a §371 filing based on International Application No. PCT/EP2011/050654, filed Jan. 19, 2011, which claims the benefit of Provisional European Patent Application Serial Number 10151805.8 filed Jan. 27, 2010. The entire contents of these patent applications are hereby incorporated herein by reference.

The present invention relates to certain sulfonamido 3,4-diarylpyrazole compounds, which modulate the activity of protein kinases. The compounds of this invention are therefore useful in treating diseases caused by deregulated protein kinase activity. The present invention also provides methods for preparing these compounds, pharmaceutical compositions comprising these compounds, and methods of treating diseases utilizing pharmaceutical compositions comprising these compounds.

The malfunctioning of protein kinases (PKs) is the hallmark of numerous diseases.

A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or disregulation see, for instance, Current Opinion in Chemical Biology 1999, 3, 459-465 and Carcinogenesis 2008, 29, 1087-191.

Among the several protein kinases known in the art, the classical Ras, Raf, MEK (mitogen activated protein kinase/extracellular signal-regulated kinase kinase), ERK (extracellular signal-regulated kinase) pathway plays a central role in the regulation of a variety of cellular functions dependent upon cellular context, including cellular proliferation, differentiation, survival, immortalization and angiogenesis (reviewed in Peyssonnaux and Eychene, Biology of the Cell, 2001, 93, 3-62). In this pathway, Raf family members are recruited to the plasma membrane upon binding to guanosine triphosphate (GTP) loaded Ras resulting in the phosphorylation and activation of Raf proteins. Activated Rafs then phosphorylate and activate MEKs, which in turn phosphorylate and activate ERKs. Upon activation, ERKs translocate from the cytoplasm to the nucleus resulting in the phosphorylation and regulation of activity of transcription factors such as Elk-I and Myc. The Ras/Raf/MEK/ERK pathway has been reported to contribute to the tumorigenic phenotype by inducing immortalization, growth factor-independent growth, insensitivity to growth-inhibitory signals, ability to invade and metastasize, by stimulating angiogenesis and by inhibiting apoptosis (reviewed in Kolch et al., Exp. Rev. Mol. Med., 2002, 4, 1-18). In fact, ERK phosphorylation is enhanced in approximately 30% of all human tumours (Hoshino et al., Oncogene, 1999, 18, 813-822). This may be a result of overexpression and/or mutation of key members of the pathway.

Three Raf serine/threonine protein kinase isoforms have been reported Raf-1/c-Raf, B-Raf and A-Raf (reviewed in Mercer and Pritchard, Biochim. Biophys. Acta, 2003, 1653, 25-40), the genes for which are thought to have arisen from gene duplication. All three Raf genes are expressed in most tissues but with differences: c-Raf is expressed ubiquitously at high levels, whereas B-Raf high-level expression is found in neuronal tissue and A-Raf in urogenital tissue. The highly homologous Raf family members have overlapping but distinct biochemical activities and biological functions (Hagemann and Rapp, Expt. Cell Res. 1999, 253, 34-46). Expression of all three Raf genes is required for normal murine development however both c-Raf and B-Raf are required to complete gestation. B-Raf −/− mice die at E12.5 due to vascular haemorrhaging caused by increased apoptosis of endothelial cells (Wojnowski et al, Nature Genet., 1997, 16, 293-297). B-Raf is reportedly the major isoform involved in cell proliferation and the primary target of oncogenic Ras. Activating 5 somatic missense mutations have been identified exclusively for B-Raf, occurring with a frequency of 66% in malignant cutaneous melanomas (Davies et al., Nature, 2002, 417, 949-954) and also present in a wide range of human cancers, including but not limited to papillary thyroid tumours (Cohen et al., J. Natl. Cancer Inst., 2003, 95, 625-627), cholangiocarcinomas (Tannapfel et al., Gut, 2003, 52, 706-712), colon and ovarian cancers (Davies et al., Nature, 10 2002, 417, 949-954). The most frequent mutation in B-Raf (80%) is a glutamic acid for valine substitution at position 600. These mutations increase the basal kinase activity of B-Raf and are thought to uncouple Raf/MEK/ERK signalling from upstream proliferation drives including Ras and growth factor receptor activation resulting in constitutive activation of ERK. Mutated B-Raf proteins are transforming in NIH3T3 cells (Davies et al., Nature, 2002, 15 417, 949-954) and melanocytes (Wellbrock et al., Cancer Res., 2004, 64, 2338-2342) and have also been shown to be essential for melanoma cell viability and transformation (Hingorani et al., Cancer Res., 2003, 63, 5198-5202). As a key driver of the Raf/MEK/ERK signalling cascade, B-Raf represents a likely point of intervention in tumours dependent on this pathway Substituted pyrazole derivatives for the treatment of cytokine-mediated diseases such as inflammation and arthritis are disclosed in WO98/52940 and WO00/31063 in the name of G.D. Searle & Co.

Hydroxyaryl-pyrazole derivatives for the treatment of cancer are disclosed in WO03/055860 in the name of Cancer Research Institute and in WO07/105,058 in the name of Pfizer Inc.

Pyrimidinyl-pyrazole derivatives for the treatment of hyperproliferative disorders such as cancer are disclosed in WO07/24843 in the name of SmithKline Beecham Corporation. Despite these developments, there is still need for effective agents for said diseases.

BRIEF DESCRIPTION OF THE DRAWINGS

The invention is also illustrated by reference to the accompanying drawings described below.

Figure 1:
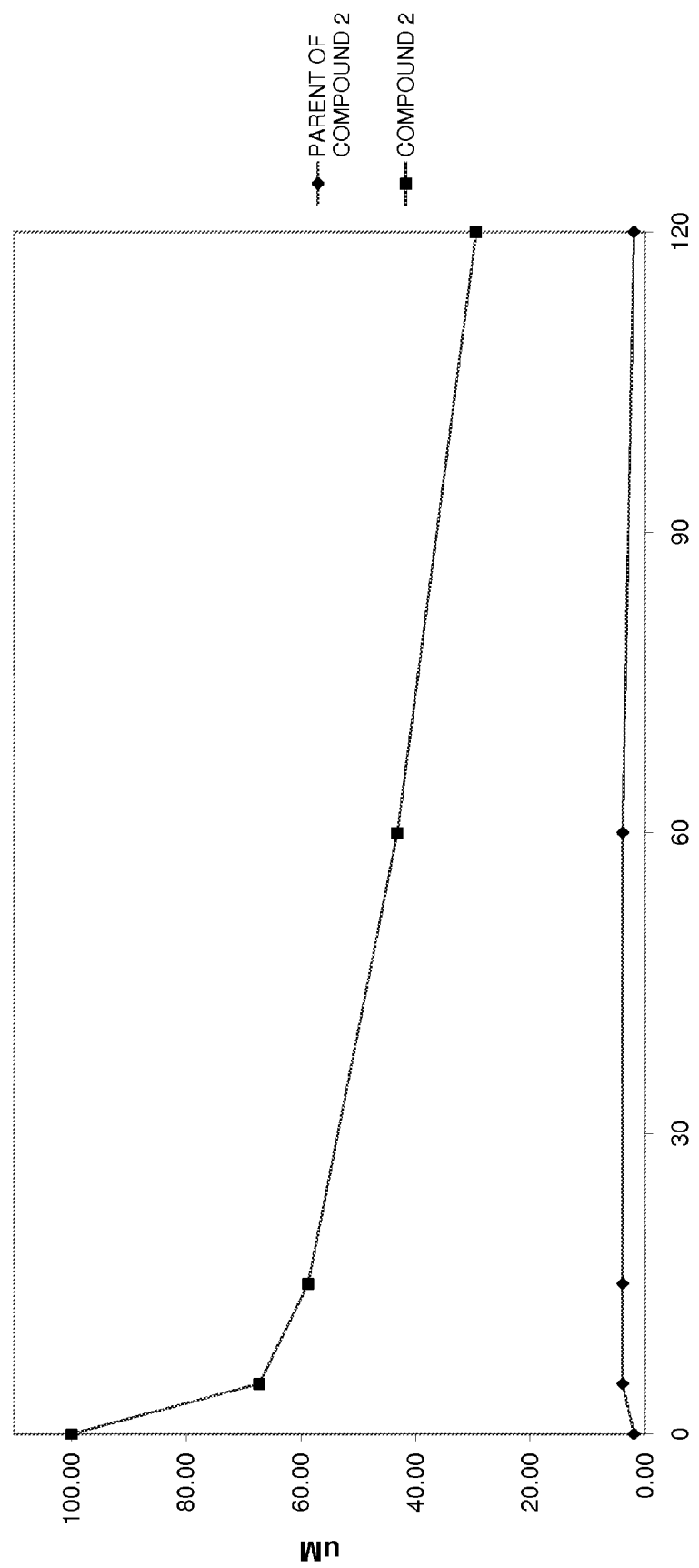
FIG. 1 refers to the stability study in buffer and shows the stability of Compound No. 2, taken as a representative of the compounds of formula (I) of the present invention, in PBS buffer pH 7.4.

The present inventors have now discovered that compounds of formula (I), described below, are kinase inhibitors and are thus useful in therapy as antitumor agents.

Accordingly, a first object of the present invention is to provide a sulfonamido 3,4-diarylpyrazole compound represented by formula (I),

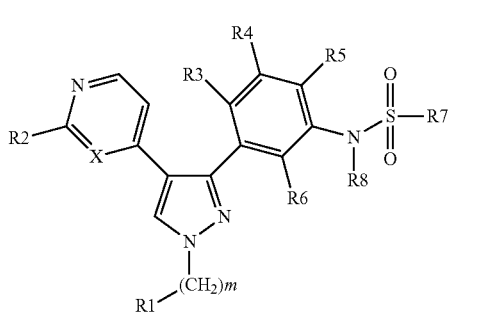

wherein:
m is an integer from 0 to 6;
R1 is hydrogen, trichloromethyl, trifluoromethyl, halogen, cyano, OH, OR9, NR10R11, NR12COR13, COOH, COOR14, CONR15R16, or a group optionally substituted selected from straight or branched ($C_1$-$C_8$) alkyl, ($C_2$-$C_8$) alkenyl, ($C_2$-$C_8$) alkynyl, ($C_3$-$C_8$) cycloalkyl, ($C_3$-$C_8$) cycloalkenyl, heterocyclyl, aryl and heteroaryl, wherein:
R9 and R14 are, each independently one from the other, a group optionally substituted selected from straight or branched ($C_1$-$C_8$) alkyl, ($C_3$-$C_8$) cycloalkyl, heterocyclyl, aryl and heteroaryl, and
R10, R11, R12, R13, R15 and R16 are, each independently one from the other, hydrogen or a group optionally substituted selected from straight or branched ($C_1$-$C_8$) alkyl, ($C_3$-$C_8$) cycloalkyl, heterocyclyl, aryl and heteroaryl, or taken together with the atoms to which they are bonded either R10 and R11 as well as R12 and R13, and R15 and R16 may form an optionally substituted heterocyclyl or heteroaryl, optionally containing one additional heteroatom or heteroatomic group selected from S, O, N and NH;
X is —CH or N;
R2 is hydrogen, halogen, NR17R18, SR19 or $SO_2$R19, wherein:
R17 and R18 are, each independently one from the other, hydrogen or a group optionally substituted selected from straight or branched ($C_1$-$C_8$) alkyl, ($C_3$-$C_8$) cycloalkyl, heterocyclyl, aryl and heteroaryl, or taken together with the nitrogen atom to which they are bonded R17 and R18 may form an optionally substituted heterocyclyl or heteroaryl, optionally containing one additional heteroatom or heteroatomic group selected from S, O, N and NH; or R17 is hydrogen and R18 is COR20,
wherein:
R20 is OR21, NR22R23 or a group optionally substituted selected from straight or branched ($C_1$-$C_8$) alkyl, ($C_2$-$C_8$) alkenyl or ($C_2$-$C_8$) alkynyl, ($C_3$-$C_8$) cycloalkyl, ($C_3$-$C_8$) cylcoalkenyl, heterocyclyl, aryl and heteroaryl, wherein:
R21 is a group optionally substituted selected from straight or branched ($C_1$-$C_8$) alkyl, ($C_3$-$C_8$) cycloalkyl, heterocyclyl, aryl and heteroaryl, and
R22 and R23 are, each independently one from the other, hydrogen or a group optionally substituted selected from straight or branched ($C_1$-$C_8$) alkyl, ($C_3$-$C_8$) cycloalkyl, heterocyclyl, aryl and heteroaryl, or taken together with the nitrogen atom to which they are bonded R22 and R23 may form an optionally
substituted heterocyclyl or heteroaryl, optionally containing one additional heteroatom or heteroatomic group selected from S, O, N or NH; and
R19 is a group optionally substituted selected from straight or branched ($C_1$-$C_8$) alkyl, ($C_3$-$C_8$) cycloalkyl, heterocyclyl, aryl and heteroaryl;
R3, R4, R5 and R6 are, each independently one from the other, hydrogen, halogen, trifluoromethyl, trichloromethyl, cyano, OR24, NR25R26, or a group optionally substituted selected from straight or branched ($C_1$-$C_8$) alkyl and ($C_3$-$C_8$) cycloalkyl, wherein:
R24 is a group optionally substituted selected from straight or branched ($C_1$-$C_8$) alkyl and ($C_3$-$C_8$) cycloalkyl, and
R25 and R26 are, each independently one from the other, hydrogen or a group optionally substituted selected from straight or branched ($C_1$-$C_8$) alkyl, ($C_3$-$C_8$) cycloalkyl, heterocyclyl, aryl and heteroaryl; or taken together with the nitrogen atom to which they are bonded R25 and R26 may form an optionally substituted heterocyclyl or heteroaryl, optionally containing one additional heteroatom or heteroatomic group selected from S, O, N and NH;
R7 is an optionally substituted group selected from straight or branched ($C_1$-$C_8$) alkyl, ($C_2$-$C_8$) alkenyl, ($C_2$-$C_8$) alkynyl, ($C_3$-$C_8$) cycloalkyl, ($C_3$-$C_8$) cylcoalkenyl, heterocyclyl, aryl and heteroaryl;
R8 is COR27 or CHR28OCOR29, wherein:
R27 is hydrogen or a group optionally substituted from straight or branched ($C_1$-$C_8$) alkyl, ($C_2$-$C_8$) alkenyl or ($C_2$-$C_8$) alkynyl, ($C_3$-$C_8$) cycloalkyl, ($C_3$-$C_8$) cycloalkenyl, heterocyclyl, aryl and heteroaryl, or a group OR30, wherein:
R30 is a group optionally substituted selected from straight or branched ($C_1$-$C_8$) alkyl, ($C_2$-$C_8$) alkenyl or ($C_2$-$C_8$) alkynyl, ($C_3$-$C_8$) cycloalkyl, ($C_3$-$C_8$) cycloalkenyl, heterocyclyl, aryl and heteroaryl;
R28 is hydrogen or an optionally substituted straight or branched ($C_1$-$C_3$) alkyl;
R29 is a group optionally substituted selected from straight or branched ($C_1$-$C_8$) alkyl, ($C_2$-$C_8$) alkenyl, ($C_2$-$C_8$) alkynyl, ($C_3$-$C_8$) cycloalkyl, ($C_3$-$C_8$) cycloalkenyl, heterocyclyl, aryl and heteroaryl, or a group NR31R32, wherein:
R31 and R32 are, each independently one from the other, hydrogen or a group optionally substituted selected from straight or branched ($C_1$-$C_8$) alkyl, ($C_3$-$C_8$) cycloalkyl, heterocyclyl, aryl and heteroaryl; or taken together with the nitrogen atom to which they are bonded R31 and R132 may form an optionally substituted heterocyclyl or heteroaryl, optionally containing one additional heteroatom or heteroatomic group selected from S, O, N and NH;
and pharmaceutically acceptable salts thereof.

The present invention also provides methods of preparing the sulfonamido 3,4-diarylpyrazole compounds, represented by formula (I), prepared through a process consisting of standard synthetic transformations.

The present invention also provides a method for treating diseases caused by and/or associated with dysregulated protein kinase activity, particularly RAF family, protein kinase C in different isoforms, Met, PAK-4, PAK-5, ZC-1, STLK-2, DDR-2, Aurora A, Aurora B, Aurora C, Bub-1, Chk1, Chk2, HER2, MEK1, MAPK, EGF-R, PDGF-R, FGF-R, IGF-R, PI3K, weel kinase, Src, Abl, Akt, MAPK, ILK, MK-2, IKK-2, Cdc7, Nek, Cdk/cyclin kinase family, including PLK-1 and PLK-3, which comprises administering to a mammal, in need thereof, an effective amount of a substituted 3,4-diarylpyrazole compound represented by formula (I) as defined above.

A preferred method of the present invention is to treat a disease caused by and/or associated with dysregulated protein kinase activity selected from the group consisting of cancer, cell proliferative disorders, viral infections, autoimmune and neurodegenerative disorders.

Another preferred method of the present invention is to treat specific types of cancer including but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Another preferred method of the present invention is to treat specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

Another preferred method of the present invention is to treat viral infections, in particular the prevention of AIDS development in HIV-infected individuals.

In addition, the method of the present invention also provides tumor angiogenesis and metastasis inhibition as well as the treatment of organ transplant rejection and host versus graft disease.

In a further preferred embodiment, the method of the present invention further comprises subjecting the mammal in need thereof to a radiation therapy or chemotherapy regimen in combination with at least one cytostatic or cytotoxic agent.

Moreover the invention provides an in vitro method for inhibiting the RAF family protein activity which comprises contacting the said protein with an effective amount of a compound of formula (I).

The present invention also provides a pharmaceutical composition comprising one or more compounds of formula (I) or a pharmaceutically acceptable salt thereof and a pharmaceutically acceptable excipient, carrier or diluent.

The present invention further provides a pharmaceutical composition comprising a compound of formula (I) in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

Additionally, the invention provides a product or kit comprising a compound of formula (I) or a pharmaceutically acceptable salt thereof, as defined above, or pharmaceutical compositions thereof and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament. Preferably the invention provides a compound of formula (I) or a pharmaceutically acceptable salt thereof, as defined above, for use as a prodrug.

Moreover the invention provides the use of a compound of formula (I) or a pharmaceutically acceptable salt thereof, as defined above, in the manufacture of a medicament with anticancer activity.

Finally, the invention provides a compound of formula (I) or a pharmaceutically acceptable salt thereof, as defined above, for use in a method of treating cancer.

Unless otherwise specified, when referring to the compounds of formula (I) per se as well as to any pharmaceutical composition thereof or to any therapeutic treatment comprising them, the present invention includes all of the isomers, tautomers, hydrates, solvates, complexes, metabolites, carriers, N-oxides and pharmaceutically acceptable salts of the compounds of this invention.

A metabolite of a compound of formula (I) is any compound into which this same compound of formula (I) is converted in vivo, for instance upon administration to a mammal in need thereof. Typically, without however representing a limiting example, upon administration of a compound of formula (I), this same derivative may be converted into a variety of compounds, for instance including more soluble derivatives like hydroxylated derivatives, which are easily excreted. Hence, depending upon the metabolic pathway thus occurring, any of these hydroxylated derivatives may be regarded as a metabolite of the compounds of formula (I).

N-oxides are compounds of formula (I) wherein nitrogen and oxygen are tethered through a dative bond.

If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases when compounds can exist in tautomeric forms, each form is contemplated as being included within this invention whether existing in equilibrium or predominantly in one form.

As such, unless otherwise provided, when in compounds of formula (I) m is 0 and R1 is hydrogen, only one of the following tautomeric forms of formula (Ia) or (Ib) is indicated, the remaining one has still to be intended as comprised within the scope of the invention:

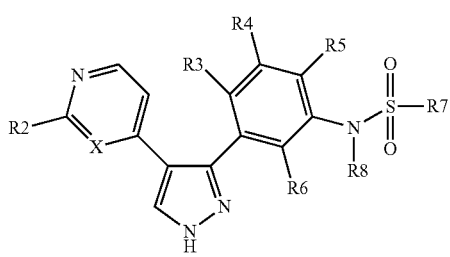

(Ia)

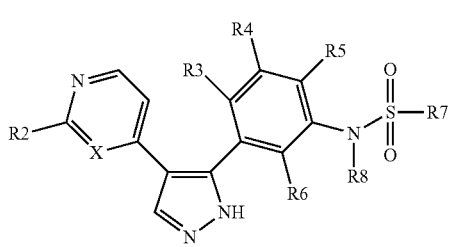

(Ib)

In cases when compounds can exist in tautomeric forms, each form is contemplated as being included within this invention whether existing in equilibrium or predominantly in one form.

In cases wherein compounds may exist in other tautomeric forms, such as keto-enol tautomers, each tautomeric form is contemplated as being included within this invention whether existing in equilibrium or predominantly in one form.

With the term "straight or branched $C_1$-$C_8$ alkyl", we intend any of the groups such as, for instance, methyl, ethyl, n-propyl, isopropyl, n-butyl, isobutyl, tert-butyl, sec-butyl, n-pentyl, n-hexyl, n-heptyl, n-octyl and the like.

With the term "straight or branched $C_1$-$C_6$ alkyl", we intend any of the groups such as, for instance, methyl, ethyl, n-propyl, isopropyl, n-butyl, isobutyl, tert-butyl, sec-butyl, n-pentyl, n-hexyl, and the like.

With the term "straight or branched $C_1$-$C_3$ alkyl", we intend any of the groups such as, for instance, methyl, ethyl, n-propyl, isopropyl.

With the term "$C_3$-$C_8$ cycloalkyl" we intend, unless otherwise provided, 3- to 8-membered all-carbon monocyclic ring, which may contain one or more double bonds but does not have a completely conjugated π-electron system. Examples of cycloalkyl groups, without limitation, are cyclopropane, cyclobutane, cyclopentane, cyclopentene, cyclohexane, cyclohexene and cyclohexadiene.

With the term "heterocyclyl" we intend a 3- to 8-membered, saturated or partially unsaturated carbocyclic ring where one or more carbon atoms are replaced by heteroatoms such as nitrogen, oxygen and sulfur. Non limiting examples of heterocyclyl groups are, for instance, pyrane, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

With the term "$C_2$-$C_8$ alkenyl" we intend an aliphatic $C_2$-$C_8$ hydrocarbon chain containing at least one carbon-carbon double bond and which can be straight or branched. Representative examples include, but are not limited to, ethenyl, 1-propenyl, 2-propenyl, 1- or 2-butenyl, and the like.

With the term "$C_2$-$C_8$ alkynyl" we intend an aliphatic $C_2$-$C_8$ hydrocarbon chain containing at least one carbon-carbon triple bond and which can be straight or branched. Representative examples include, but are not limited to, ethynyl, 1-propynyl, 2-propynyl, 1- or 2-butynyl, and the like.

The term "aryl" refers to a mono-, bi- or poly-carbocyclic hydrocarbon with from 1 to 4 ring systems, optionally further fused or linked to each other by single bonds, wherein at least one of the carbocyclic rings is "aromatic", wherein the term "aromatic" refers to completely conjugated π-electron bond system. Non-limiting examples of such aryl groups are phenyl, α- or β-naphthyl or biphenyl groups.

The term "heteroaryl" refers to aromatic heterocyclic rings, typically 5- to 8-membered heterocycles with from 1 to 3 heteroatoms selected among N, O or S; the heteroaryl ring can be optionally further fused or linked to aromatic and non-aromatic carbocyclic and heterocyclic rings. Not limiting examples of such heteroaryl groups are, for instance, pyridyl, pyrazinyl, pyrimidinyl, pyridazinyl, indolyl, imidazolyl, thiazolyl, isothiazolyl, pyrrolyl, phenyl-pyrrolyl, furyl, phenyl-furyl, oxazolyl, isoxazolyl, pyrazolyl, thienyl, benzothienyl, isoindolinyl, benzoimidazolyl, quinolinyl, isoquinolinyl, 1,2,3-triazolyl, 1-phenyl-1,2,3-triazolyl, 2,3-dihydroindolyl, 2,3-dihydrobenzofuranyl, 2,3-dihydrobenzothiophenyl; benzopyranyl, 2,3-dihydrobenzoxazinyl, 2,3-dihydroquinoxalinyl and the like.

According to the present invention and unless otherwise provided, the phrase "optionally substituted" applied to any of the groups defined above, means that such groups may be optionally substituted in any of their free positions, by one or more groups, for instance 1 to 6 groups, independently selected from: halogen, nitro, oxo groups (=O), cyano, $C_1$-$C_8$ alkyl, polyfluorinated alkyl, polyfluorinated alkoxy, $C_2$-$C_8$ alkenyl, $C_2$-$C_8$ alkynyl, hydroxyalkyl, aryl, arylalkyl, heteroaryl, heteroarylalkyl, heterocyclyl, heterocyclylalkyl, $C_3$-$C_8$ cycloalkyl, hydroxy, alkoxy, aryloxy, heterocyclyloxy, methylenedioxy, alkylcarbonyloxy, arylcarbonyloxy, cycloalkenyloxy, heterocyclylcarbonyloxy, alkylideneaminooxy, carboxy, alkoxycarbonyl, aryloxycarbonyl, cycloalkyloxycarbonyl, heterocyclylalkyloxycarbonyl, amino, ureido, alkylamino, dialkylamino, arylamino, diarylamino, heterocyclylamino, formylamino, alkylcarbonylamino, arylcarbonylamino, heterocyclylcarbonylamino, aminocarbonyl, alkylaminocarbonyl, dialkylaminocarbonyl, arylaminocarbonyl, heterocyclylaminocarbonyl, alkoxycarbonylamino, hydroxyaminocarbonyl alkoxyimino, alkylsulfonylamino, arylsulfonylamino, heterocyclylsulfonylamino, formyl, alkylcarbonyl, arylcarbonyl, cycloalkylcarbonyl, heterocyclylcarbonyl, alkylsulfonyl, arylsulfonyl, aminosulfonyl, alkylaminosulfonyl, dialkylaminosulfonyl, arylaminosulfonyl, heterocyclylaminosulfonyl, arylthio, alkylthio, phosphonate and alkylphosphonate. In their turn, whenever appropriate, each of the above substituent may be further substituted by one or more of the aforementioned groups.

With the term halogen atom we intend a fluorine, chlorine, bromine or iodine atom.

With the term cyano we intend a —CN residue.

With the term nitro we intend a —NO$_2$ group.

With the term polyfluorinated alkyl or polyfluorinated alkoxy we intend any of the above straight or branched $C_1$-$C_8$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term hydroxyalkyl we intend any of the above $C_1$-$C_8$ alkyl, bearing an hydroxyl group such as, for instance, hydroxymethyl, 2-hydroxyethyl, 3-hydroxypropyl and the like.

From all of the above, it is clear to the skilled person that any group which name is a composite name such as, for instance, arylamino has to be intended as conventionally construed by the parts from which it derives, e.g. by an amino group which is further substituted by aryl, wherein aryl is as above defined.

Likewise, any of the terms such as, for instance, alkylthio, alkylamino, dialkylamino, alkoxycarbonyl, alkoxycarbonylamino, heterocyclylcarbonyl, heterocyclylcarbonylamino, cycloalkyloxycarbonyl and the like, include groups wherein the alkyl, alkoxy, aryl, $C_3$-$C_8$ cycloalkyl and heterocyclyl moieties are as above defined.

Pharmaceutically acceptable salts of the compounds of formula (I) include the acid addition salts with inorganic or organic acids, e.g., nitric, hydrochloric, hydrobromic, sulfuric, perchloric, phosphoric, acetic, trifluoroacetic, propionic, glycolic, lactic, oxalic, fumaric, malonic, malic, maleic, tartaric, citric, benzoic, cinnamic, mandelic, methanesulphonic, isethionic and salicylic acid.

Pharmaceutically acceptable salts of the compounds of formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines, preferably methylamine, ethylamine, diethylamine, triethylamine, piperidine and the like.

A preferred class of compounds of formula (I) are the compounds wherein:
m is 1 or 2.

Another preferred class of compounds of formula (I) are the compounds wherein:
R1 is hydrogen, trichloromethyl, trifluoromethyl, halogen, cyano, OH, OR9, NR12COR13, CONR15R16, or a group optionally substituted selected from straight or branched ($C_1$-$C_8$) alkyl, ($C_2$-$C_8$) alkenyl, ($C_2$-$C_8$) alkynyl, ($C_3$-$C_8$) cycloalkyl, ($C_3$-$C_8$) cycloalkenyl, heterocyclyl, aryl and heteroaryl, wherein:
R9, R12, R13, R15 and R16 are as defined above.

A further preferred class of compounds of formula (I) are the compounds wherein:
R3, R4, R5 and R6 are, each independently one from the other, hydrogen, halogen, trifluoromethyl, trichloromethyl, or a group optionally substituted selected from straight or branched ($C_1$-$C_8$) alkyl and ($C_3$-$C_8$) cycloalkyl.

Another further preferred class of compounds of formula (I) are the compounds wherein:
R7 is an optionally substituted group selected from straight or branched ($C_1$-$C_8$) alkyl, ($C_3$-$C_8$) cycloalkyl, ($C_3$-$C_8$) cycloalkenyl, heterocyclyl, aryl and heteroaryl.

A particularly preferred class of compounds of formula (I) are the compounds wherein:
R1 is hydrogen, trichloromethyl, trifluoromethyl, halogen or cyano.

Preferred compounds of formula (I) are the compounds listed below:

1) methyl [(2,5-difluorophenyl)sulfonyl]{3-[1-ethyl-4-(pyridin-4-yl)-1H-pyrazol-3-yl]-2,4-difluorophenyl}carbamate,
2) ethyl [(2,5-difluorophenyl)sulfonyl]{3-[1-ethyl-4-(pyridin-4-yl)-1H-pyrazol-3-yl]-2,4-difluorophenyl}carbamate,
3) propyl [(2,5-difluorophenyl)sulfonyl]{3-[1-ethyl-4-(pyridin-4-yl)-1H-pyrazol-3-yl]-2,4-difluorophenyl}carbamate,
4) propan-2-yl [(2,5-difluorophenyl)sulfonyl]{3-[1-ethyl-4-(pyridin-4-yl)-1H-pyrazol-3-yl]-2,4-difluorophenyl}carbamate,
5) N-[(2,5-difluorophenyl)sulfonyl]-N-{3-[1-ethyl-4-(pyridin-4-yl)-1H-pyrazol-3-yl]-2,4-difluorophenyl}acetamide,
6) N-[(2,5-difluorophenyl)sulfonyl]-N-{3-[1-ethyl-4-(pyridin-4-yl)-1H-pyrazol-3-yl]-2,4-difluorophenyl}-N2,N2-dimethylglycinamide,
7) ([(2,5-difluorophenyl)sulfonyl]{3-[1-ethyl-4-(pyridin-4-yl)-1H-pyrazol-3-yl]-2,4-difluorophenyl}amino)methyl acetate,
8) ([(2,5-difluorophenyl)sulfonyl]{3-[1-ethyl-4-(pyridin-4-yl)-1H-pyrazol-3-yl]-2,4-difluorophenyl}amino)methyl benzoate,
9) ([(2,5-difluorophenyl)sulfonyl]{3-[1-ethyl-4-(pyridin-4-yl)-1H-pyrazol-3-yl]-2,4-difluorophenyl}amino)methyl N,N-dimethylglycinate,
10) ethyl N-{[([(2,5-difluorophenyl)sulfonyl]{3-[1-ethyl-4-(pyridin-4-yl)-1H-pyrazol-3-yl]-2,4-difluorophenyl}amino) methoxy]carbonyl}-N-methylglycinate,
11) methyl [(2,5-difluorophenyl)sulfonyl]{3-[1-methyl-4-(pyridin-4-yl)-1H-pyrazol-3-yl]-2,4-difluorophenyl}carbamate,
12) ethyl [(2,5-difluorophenyl)sulfonyl]{3-[1-methyl-4-(pyridin-4-yl)-1H-pyrazol-3-yl]-2,4-difluorophenyl}carbamate,
13) propyl [(2,5-difluorophenyl)sulfonyl]{3-[1-methyl-4-(pyridin-4-yl)-1H-pyrazol-3-yl]-2,4-difluorophenyl}carbamate,
14) propan-2-yl [(2,5-difluorophenyl)sulfonyl]{3-[1-methyl-4-(pyridin-4-yl)-1H-pyrazol-3-yl]-2,4-difluorophenyl}carbamate,
15) N-[(2,5-difluorophenyl)sulfonyl]-N-{3-[1-methyl-4-(pyridin-4-yl)-1H-pyrazol-3-yl]-2,4-difluorophenyl}acetamide,
16) N-[(2,5-difluorophenyl)sulfonyl]-N-{3-[1-methyl-4-(pyridin-4-yl)-1H-pyrazol-3-yl]-2,4-difluorophenyl}-N2,N2-dimethylglycinamide,
17) ([(2,5-difluorophenyl)sulfonyl]{3-[1-methyl-4-(pyridin-4-yl)-1H-pyrazol-3-yl]-2,4-difluorophenyl}amino)methyl acetate,
18) ([(2,5-difluorophenyl)sulfonyl]{3-[1-methyl-4-(pyridin-4-yl)-1H-pyrazol-3-yl]-2,4-difluorophenyl}amino)methyl benzoate,
19) ([(2,5-difluorophenyl)sulfonyl]{3-[1-methyl-4-(pyridin-4-yl)-1H-pyrazol-3-yl]-2,4-difluorophenyl}amino)methyl N,N-dimethylglycinate,
20) ethyl N-{[([(2,5-difluorophenyl)sulfonyl]{3-[1-methyl-4-(pyridin-4-yl)-1H-pyrazol-3-yl]-2,4-difluorophenyl}amino)methoxy]carbonyl}-N-methylglycinate,
21) methyl {3-[1-ethyl-4-(pyridin-4-yl)-1H-pyrazol-3-yl]-2,4-difluorophenyl}[(3-fluorophenyl)sulfonyl]carbamate,
22) ethyl {3-[1-ethyl-4-(pyridin-4-yl)-1H-pyrazol-3-yl]-2,4-difluorophenyl}[(3-fluorophenyl)sulfonyl]carbamate,
23) propyl {3-[1-ethyl-4-(pyridin-4-yl)-1H-pyrazol-3-yl]-2,4-difluorophenyl}[(3-fluorophenyl)sulfonyl]carbamate,
24) propan-2-yl {3-[1-ethyl-4-(pyridin-4-yl)-1H-pyrazol-3-yl]-2,4-difluorophenyl}[(3-fluorophenyl)sulfonyl]carbamate,
25) N-{3-[1-ethyl-4-(pyridin-4-yl)-1H-pyrazol-3-yl]-2,4-difluorophenyl}-N-[(3-fluorophenyl)sulfonyl]acetamide,
26) N-{3-[1-ethyl-4-(pyridin-4-yl)-1H-pyrazol-3-yl]-2,4-difluorophenyl}-N-[(3 fluorophenyl)sulfonyl]-N2,N2-dimethylglycinamide,
27) ({3-[1-ethyl-4-(pyridin-4-yl)-1H-pyrazol-3-yl]-2,4-difluorophenyl}[(3-fluorophenyl)sulfonyl]amino)methyl acetate,
28) ({3-[1-ethyl-4-(pyridin-4-yl)-1H-pyrazol-3-yl]-2,4-difluorophenyl}[(3-fluorophenyl)sulfonyl]amino)methyl benzoate, 29) ({3-[1-ethyl-4-(pyridin-4-yl)-1H-pyrazol-3-yl]-2,4-difluorophenyl}[(3-fluorophenyl)sulfonyl]amino)methyl N,N-dimethylglycinate,
30) ethyl N-{[({3-[1-ethyl-4-(pyridin-4-yl)-1H-pyrazol-3-yl]-2,4-difluorophenyl}[(3-fluorophenyl) sulfonyl]amino)methoxy]carbonyl}-N-methylglycinate,
31) methyl {3-[1-ethyl-4-(pyridin-4-yl)-1H-pyrazol-3-yl]-2,4-difluorophenyl}[(2-fluorophenyl)sulfonyl]carbamate,
32) ethyl {3-[1-ethyl-4-(pyridin-4-yl)-1H-pyrazol-3-yl]-2,4-difluorophenyl}[(2-fluorophenyl)sulfonyl]carbamate,
33) propyl {3-[1-ethyl-4-(pyridin-4-yl)-1H-pyrazol-3-yl]-2,4-difluorophenyl}[(2-fluorophenyl)sulfonyl]carbamate,
34) propan-2-yl {3-[1-ethyl-4-(pyridin-4-yl)-1H-pyrazol-3-yl]-2,4-difluorophenyl}[(2-fluorophenyl)sulfonyl]carbamate,
35) N-{3-[1-ethyl-4-(pyridin-4-yl)-1H-pyrazol-3-yl]-2,4-difluorophenyl}-N-[(2-fluorophenyl)sulfonyl]acetamide,
36) N-{3-[1-ethyl-4-(pyridin-4-yl)-1H-pyrazol-3-yl]-2,4-difluorophenyl}-N-[(2-fluorophenyl)sulfonyl]-N2,N2-dimethylglycinamide,
37) ({3-[1-ethyl-4-(pyridin-4-yl)-1H-pyrazol-3-yl]-2,4-difluorophenyl}[(2-fluorophenyl)sulfonyl]amino)methyl acetate,
38) ({3-[1-ethyl-4-(pyridin-4-yl)-1H-pyrazol-3-yl]-2,4-difluorophenyl}[(2-fluorophenyl)sulfonyl]amino)methyl benzoate,
39) ({3-[1-ethyl-4-(pyridin-4-yl)-1H-pyrazol-3-yl]-2,4-difluorophenyl}[(2-fluorophenyl)sulfonyl]amino)methyl N,N-dimethylglycinate,
40) ethyl N-{[({3-[1-ethyl-4-(pyridin-4-yl)-1H-pyrazol-3-yl]-2,4-difluorophenyl}[(2-fluorophenyl)sulfonyl]amino)methoxy]carbonyl}-N-methylglycinate,
41) methyl {3-[4-(2-aminopyridin-4-yl)-1-ethyl-1H-pyrazol-3-yl]-2,4-difluorophenyl}[(2,5-difluorophenyl) sulfonyl]carbamate,
42) ethyl {3-[4-(2-aminopyridin-4-yl)-1-ethyl-1H-pyrazol-3-yl]-2,4-difluorophenyl}[(2,5-difluorophenyl) sulfonyl]carbamate,
43) propyl {3-[4-(2-aminopyridin-4-yl)-1-ethyl-1H-pyrazol-3-yl]-2,4-difluorophenyl}[(2,5-difluorophenyl) sulfonyl]carbamate,
44) propan-2-yl {3-[4-(2-aminopyridin-4-yl)-1-ethyl-1H-pyrazol-3-yl]-2,4-difluorophenyl}[(2,5-difluorophenyl)sulfonyl]carbamate,
45) N-{3-[4-(2-aminopyridin-4-yl)-1-ethyl-1H-pyrazol-3-yl]-2,4-difluorophenyl}-N-(2,5-difluorophenyl) sulfonyl]acetamide,
46) N-{3-[4-(2-aminopyridin-4-yl)-1-ethyl-1H-pyrazol-3-yl]-2,4-difluorophenyl}-N-[(2,5-difluorophenyl) sulfonyl]-N2,N2-dimethylglycinamide,
47) ({3-[4-(2-aminopyridin-4-yl)-1-ethyl-1H-pyrazol-3-yl]-2,4-difluorophenyl}[(2,5-difluorophenyl)sulfonyl]amino) methyl acetate,
48) ({3-[4-(2-aminopyridin-4-yl)-1-ethyl-1H-pyrazol-3-yl]-2,4-difluorophenyl}[(2,5-difluorophenyl)sulfonyl]amino) methyl benzoate,
49) ({3-[4-(2-aminopyridin-4-yl)-1-ethyl-1H-pyrazol-3-yl]-2,4-difluorophenyl}[(2,5-difluorophenyl)sulfonyl]amino) methyl N,N-dimethylglycinate,
50) ethyl N-{[({3-[4-(2-aminopyridin-4-yl)-1-ethyl-1H-pyrazol-3-yl]-2,4-difluorophenyl}[(2,5-difluorophenyl) sulfonyl]amino)methoxy]carbonyl}-N-methylglycinate,
51) methyl [(2,5-difluorophenyl)sulfonyl]{3-[1-ethyl-4-(pyridin-4-yl)-1H-pyrazol-3-yl]-4-fluorophenyl}carbamate,
52) ethyl [(2,5-difluorophenyl)sulfonyl]{3-[1-ethyl-4-(pyridin-4-yl)-1H-pyrazol-3-yl]-4-fluorophenyl}carbamate,
53) propyl [(2,5-difluorophenyl)sulfonyl]{3-[1-ethyl-4-(pyridin-4-yl)-1H-pyrazol-3-yl]-4-fluorophenyl}carbamate,
54) propan-2-yl [(2,5-difluorophenyl)sulfonyl]{3-[1-ethyl-4-(pyridin-4-yl)-1H-pyrazol-3-yl]-4-fluorophenyl}carbamate,
55) N-[(2,5-difluorophenyl)sulfonyl]-N-{3-[1-ethyl-4-(pyridin-4-yl)-1H-pyrazol-3-yl]-4-fluorophenyl}acetamide,
56) N-[(2,5-difluorophenyl)sulfonyl]-N-{3-[1-ethyl-4-(pyridin-4-yl)-1H-pyrazol-3-yl]-4-fluorophenyl}-N2,N2-dimethylglycinamide,
57) ([(2,5-difluorophenyl)sulfonyl]{3-[1-ethyl-4-(pyridin-4-yl)-1H-pyrazol-3-yl]-4-fluorophenyl}amino)methyl acetate,
58) ([(2,5-difluorophenyl)sulfonyl]{3-[1-ethyl-4-(pyridin-4-yl)-1H-pyrazol-3-yl]-4-fluorophenyl}amino)methyl benzoate,
59) ([(2,5-difluorophenyl)sulfonyl]{3-[1-ethyl-4-(pyridin-4-yl)-1H-pyrazol-3-yl]-4-fluorophenyl}amino)methyl N,N-dimethylglycinate,
60) ethyl N-{[([(2,5-difluorophenyl)sulfonyl]{3-[1-ethyl-4-(pyridin-4-yl)-1H-pyrazol-3-yl]-4-fluorophenyl}amino) methoxy]carbonyl}-N-methylglycinate,
61) methyl [(2,5-difluorophenyl)sulfonyl]{3-[1-ethyl-4-(pyridin-4-yl)-1H-pyrazol-3-yl]-2-fluorophenyl}carbamate,
62) ethyl [(2,5-difluorophenyl)sulfonyl]{3-[1-ethyl-4-(pyridin-4-yl)-1H-pyrazol-3-yl]-2-fluorophenyl}carbamate,
63) propyl [(2,5-difluorophenyl)sulfonyl]{3-[1-ethyl-4-(pyridin-4-yl)-1H-pyrazol-3-yl]-2-fluorophenyl}carbamate,
64) propan-2-yl [(2,5-difluorophenyl)sulfonyl]{3-[1-ethyl-4-(pyridin-4-yl)-1H-pyrazol-3-yl]-2-fluorophenyl}carbamate,
65) N-[(2,5-difluorophenyl)sulfonyl]-N-{3-[1-ethyl-4-(pyridin-4-yl)-1H-pyrazol-3-yl]-2-fluorophenyl}acetamide,
66) N-[(2,5-difluorophenyl)sulfonyl]-N-{3-[1-ethyl-4-(pyridin-4-yl)-1H-pyrazol-3-yl]-2-fluorophenyl}-N2,N2-dimethylglycinamide,
67) ([(2,5-difluorophenyl)sulfonyl]{3-[1-ethyl-4-(pyridin-4-yl)-1H-pyrazol-3-yl]-2-fluorophenyl}amino)methyl acetate,
68) ([(2,5-difluorophenyl)sulfonyl]{3-[1-ethyl-4-(pyridin-4-yl)-1H-pyrazol-3-yl]-2-fluorophenyl}amino)methyl benzoate,
69) ([(2,5-difluorophenyl)sulfonyl]{3-[1-ethyl-4-(pyridin-4-yl)-1H-pyrazol-3-yl]-2-fluorophenyl}amino)methyl N,N-dimethylglycinate,
70) ethyl N-{[([(2,5-difluorophenyl)sulfonyl]{3-[1-ethyl-4-(pyridin-4-yl)-1H-pyrazol-3-yl]-2-fluorophenyl}amino) methoxy]carbonyl}-N-methylglycinate,
71) methyl [(2,5-difluorophenyl)sulfonyl]{3-[1-ethyl-4-(pyridin-4-yl)-1H-pyrazol-3-yl]-2-methylphenyl}carbamate,
72) ethyl [(2,5-difluorophenyl)sulfonyl]{3-[1-ethyl-4-(pyridin-4-yl)-1H-pyrazol-3-yl]-2-methylphenyl}carbamate,
73) propyl [(2,5-difluorophenyl)sulfonyl]{3-[1-ethyl-4-(pyridin-4-yl)-1H-pyrazol-3-yl]-2-methylphenyl}carbamate,
74) propan-2-yl [(2,5-difluorophenyl)sulfonyl]{3-[1-ethyl-4-(pyridin-4-yl)-1H-pyrazol-3-yl]-2-methylphenyl}carbamate,
75) N-[(2,5-difluorophenyl)sulfonyl]-N-{3-[1-ethyl-4-(pyridin-4-yl)-1H-pyrazol-3-yl]-2-methylphenyl}acetamide,
76) N-[(2,5-difluorophenyl)sulfonyl]-N-{3-[1-ethyl-4-(pyridin-4-yl)-1H-pyrazol-3-yl]-2-methylphenyl}-N2,N2-dimethylglycinamide,
77) ([(2,5-difluorophenyl)sulfonyl]{3-[1-ethyl-4-(pyridin-4-yl)-1H-pyrazol-3-yl]-2-methylphenyl}amino) methyl acetate, 78) ([(2,5-difluorophenyl)sulfonyl]{3-[1-ethyl-4-(pyridin-4-yl)-1H-pyrazol-3-yl]-2-methylphenyl}amino) methyl benzoate,
79) ([(2,5-difluorophenyl)sulfonyl]{3-[1-ethyl-4-(pyridin-4-yl)-1H-pyrazol-3-yl]-2-methylphenyl}amino) methyl N,N-dimethylglycinate,
80) ethyl N-{[([(2,5-difluorophenyl)sulfonyl]{3-[1-ethyl-4-(pyridin-4-yl)-1H-pyrazol-3-yl]-2-methylphenyl}amino)methoxy]carbonyl}-N-methylglycinate,
81) methyl {3-[4-(2-aminopyrimidin-4-yl)-1-ethyl-1H-pyrazol-3-yl]-2,4-difluorophenyl}[(2,5-difluorophenyl) sulfonyl]carbamate,
82) ethyl {3-[4-(2-aminopyrimidin-4-yl)-1-ethyl-1H-pyrazol-3-yl]-2,4-difluorophenyl}[(2,5-difluorophenyl) sulfonyl]carbamate,
83) propyl {3-[4-(2-aminopyrimidin-4-yl)-1-ethyl-1H-pyrazol-3-yl]-2,4-difluorophenyl}[(2,5-difluorophenyl) sulfonyl]carbamate,
84) propan-2-yl{3-[4-(2-aminopyrimidin-4-yl)-1-ethyl-1H-pyrazol-3-yl]-2,4-difluorophenyl}[(2,5-difluorophenyl) sulfonyl]carbamate,
85) N-{3-[4-(2-aminopyrimidin-4-yl)-1-ethyl-1H-pyrazol-3-yl]-2,4-difluorophenyl}-N-[(2,5-difluorophenyl) sulfonyl]acetamide,
86) N-{3-[4-(2-aminopyrimidin-4-yl)-1-ethyl-1H-pyrazol-3-yl]-2,4-difluorophenyl}-N-[(2,5-difluorophenyl)sulfonyl]-N2,N2-dimethylglycinamide,
87) ({3-[4-(2-aminopyrimidin-4-yl)-1-ethyl-1H-pyrazol-3-yl]-2,4-difluorophenyl}[(2,5-difluorophenyl) sulfonyl] amino)methyl acetate,
88) ({3-[4-(2-aminopyrimidin-4-yl)-1-ethyl-1H-pyrazol-3-yl]-2,4-difluorophenyl}[(2,5-difluorophenyl) sulfonyl] amino)methyl benzoate,
89) ({3-[4-(2-aminopyrimidin-4-yl)-1-ethyl-1H-pyrazol-3-yl]-2,4-difluorophenyl}[(2,5-difluorophenyl) sulfonyl] amino)methyl N,N-dimethylglycinate,
90) ethyl N-{[({3-[4-(2-aminopyrimidin-4-yl)-1-ethyl-1H-pyrazol-3-yl]-2,4-difluorophenyl}[(2,5-difluorophenyl) sulfonyl]amino)methoxy]carbonyl}-N-methylglycinate,
91) methyl {3-[4-(2-aminopyrimidin-4-yl)-1-ethyl-1H-pyrazol-3-yl]-2-fluorophenyl}[(2,5-difluorophenyl) sulfonyl] carbamate,
92) ethyl {3-[4-(2-aminopyrimidin-4-yl)-1-ethyl-1H-pyrazol-3-yl]-2-fluorophenyl}[(2,5-difluorophenyl) sulfonyl] carbamate,
93) propyl {3-[4-(2-aminopyrimidin-4-yl)-1-ethyl-1H-pyrazol-3-yl]-2-fluorophenyl}[(2,5-difluorophenyl) sulfonyl] carbamate,
94) propan-2-yl{3-[4-(2-aminopyrimidin-4-yl)-1-ethyl-1H-pyrazol-3-yl]-2fluorophenyl}[(2,5-difluorophenyl) sulfonyl]carbamate,
95) N-{3-[4-(2-aminopyrimidin-4-yl)-1-ethyl-1H-pyrazol-3-yl]-2-fluorophenyl}-N-[(2,5-difluorophenyl) sulfonyl] acetamide,
96) N-{3-[4-(2-aminopyrimidin-4-yl)-1-ethyl-1H-pyrazol-3-yl]-2-fluorophenyl}-N-[(2,5-difluorophenyl)sulfonyl]-N2,N2-dimethylglycinamide,
97) ({3-[4-(2-aminopyrimidin-4-yl)-1-ethyl-1H-pyrazol-3-yl]-2-fluorophenyl}[(2,5-difluorophenyl)sulfonyl]amino) methyl acetate,
98) ({3-[4-(2-aminopyrimidin-4-yl)-1-ethyl-1H-pyrazol-3-yl]-2-fluorophenyl}[(2,5-difluorophenyl)sulfonyl]amino) methyl benzoate,
99) ({3-[4-(2-aminopyrimidin-4-yl)-1-ethyl-1H-pyrazol-3-yl]-2-fluorophenyl}[(2,5-difluorophenyl)sulfonyl]amino) methyl N,N-dimethylglycinate,
100) ethyl N-{[({3-[4-(2-aminopyrimidin-4-yl)-1-ethyl-1H-pyrazol-3-yl]-2-fluorophenyl}[(2,5-difluorophenyl) sulfonyl]amino)methoxy]carbonyl}-N-methylglycinate,
101) methyl {2,4-difluoro-3-[1-(2-fluoroethyl)-4-(pyridin-4-yl)-1H-pyrazol-3-yl]phenyl}[(2,5-difluorophenyl) sulfonyl]carbamate,
102) ethyl {2,4-difluoro-3-[1-(2-fluoroethyl)-4-(pyridin-4-yl)-1H-pyrazol-3-yl]phenyl}[(2,5-difluorophenyl) sulfonyl]carbamate,
103) propyl {2,4-difluoro-3-[1-(2-fluoroethyl)-4-(pyridin-4-yl)-1H-pyrazol-3-yl]phenyl}[(2,5-difluorophenyl) sulfonyl]carbamate,
104) propan-2-yl {2,4-difluoro-3-[1-(2-fluoroethyl)-4-(pyridin-4-yl)-1H-pyrazol-3-yl]phenyl}[(2,5-difluorophenyl) sulfonyl]carbamate,
105) N{2,4-difluoro-3-[1-(2-fluoroethyl)-4-(pyridin-4-yl)-1H-pyrazol-3-yl]phenyl}-N-[(2,5-difluorophenyl) sulfonyl]acetamide,
106) N-{2,4-difluoro-3-[1-(2-fluoroethyl)-4-(pyridin-4-yl)-1H-pyrazol-3-yl]phenyl}-N-[(2,5-difluorophenyl)sulfonyl]-N2,N2-dimethylglycinamide,
107) ({2,4-difluoro-3-[1-(2-fluoroethyl)-4-(pyridin-4-yl)-1H-pyrazol-3-yl]phenyl}[(2,5-difluorophenyl) sulfonyl] amino)methyl acetate,
108) ({2,4-difluoro-3-[1-(2-fluoroethyl)-4-(pyridin-4-yl)-1H-pyrazol-3-yl]phenyl}[(2,5-difluorophenyl) sulfonyl] amino)methyl benzoate,
109) ({2,4-difluoro-3-[1-(2-fluoroethyl)-4-(pyridin-4-yl)-1H-pyrazol-3-yl]phenyl}[(2,5-difluorophenyl) sulfonyl] amino)methyl N,N-dimethylglycinate,
110) ethyl N-{[({2,4-difluoro-3-[1-(2-fluoroethyl)-4-(pyridin-4-yl)-1H-pyrazol-3-yl]phenyl}[(2,5-difluorophenyl) sulfonyl]amino)methoxy]carbonyl}-N-methylglycinate,
111) methyl {3-[4-(2-aminopyrimidin-4-yl)-1-(2-fluoroethyl)-1H-pyrazol-3-yl]-2,4-difluorophenyl}[(2,5-difluorophenyl) sulfonyl]carbamate,
112) ethyl {3-[4-(2-aminopyrimidin-4-yl)-1-(2-fluoroethyl)-1H-pyrazol-3-yl]-2,4-difluorophenyl}[(2,5-difluorophenyl) sulfonyl]carbamate,
113) propyl {3-[4-(2-aminopyrimidin-4-yl)-1-(2-fluoroethyl)-1H-pyrazol-3-yl]-2,4-difluorophenyl}[(2,5-difluorophenyl),sulfonyl]carbamate,
114) propan-2-yl {3-[4-(2-aminopyrimidin-4-yl)-1-(2-fluoroethyl)-1H-pyrazol-3-yl]-2,4-difluorophenyl}[(2,5-difluorophenyl)sulfonyl]carbamate,
115) N-{3-[4-(2-aminopyrimidin-4-yl)-1-(2-fluoroethyl)-1H-pyrazol-3-yl]-2,4-difluorophenyl}-N-[(2,5-difluorophenyl)sulfonyl]acetamide,
116) N-{3-[4-(2-aminopyrimidin-4-yl)-1-(2-fluoroethyl)-1H-pyrazol-3-yl]-2,4-difluorophenyl}-N-[(2,5-difluorophenyl)sulfonyl]-N2,N2-dimethylglycinamide,
117) ({3-[4-(2-aminopyrimidin-4-yl)-1-(2-fluoroethyl)-1H-pyrazol-3-yl]-2,4-difluorophenyl}[(2,5-difluorophenyl) sulfonyl]amino)methyl acetate,
118) ({3-[4-(2-aminopyrimidin-4-yl)-1-(2-fluoroethyl)-1H-pyrazol-3-yl]-2,4-difluorophenyl}[(2,5-difluorophenyl) sulfonyl]amino)methyl benzoate,
119) ({3-[4-(2-aminopyrimidin-4-yl)-1-(2-fluoroethyl)-1H-pyrazol-3-yl]-2,4-difluorophenyl}[(2,5-difluorophenyl) sulfonyl]amino)methyl N,N-dimethylglycinate,
120) ethyl N-{[({3-[4-(2-aminopyrimidin-4-yl)-1-(2-fluoroethyl)-1H-pyrazol-3-yl]-2,4-difluorophenyl}[(2,5-difluorophenyl)sulfonyl]amino)methoxy]carbonyl}-N-methylglycinate,
121) methyl [(2,5-difluorophenyl)sulfonyl](2,4-difluoro-3-{1-[2-(piperidin-1-yl)ethyl]-4-(pyridin-4-yl)-1H-pyrazol-3-yl}phenyl)carbamate, 122) ethyl [(2,5-difluorophenyl)sulfonyl](2,4-difluoro-3-{1-[2-(piperidin-1-yl)ethyl]-4-(pyridin-4-yl)-1H-pyrazol-3-yl}phenyl)carbamate,
123) propyl [(2,5-difluorophenyl)sulfonyl](2,4-difluoro-3-{1-[2-(piperidin-1-yl)ethyl]-4-(pyridin-4-yl)-1H-pyrazol-3-yl}phenyl)carbamate,
124) propan-2-yl [(2,5-difluorophenyl)sulfonyl](2,4-difluoro-3-{1-[2-(piperidin-1-yl)ethyl]-4-(pyridin-4-yl)-1H-pyrazol-3-yl}phenyl)carbamate,
125) N-[(2,5-difluorophenyl)sulfonyl]-N-(2,4-difluoro-3-{1-[2-(piperidin-1-yl)ethyl]-4-(pyridin-4-yl)-1H-pyrazol-3-yl}phenyl)acetamide,
126) N-[(2,5-difluorophenyl)sulfonyl]-N-(2,4-difluoro-3-{1-[2-(piperidin-1-yl)ethyl]-4-(pyridin-4-yl)-1H-pyrazol-3-yl}phenyl)-N2,N2-dimethylglycinamide,
127) {[(2,5-difluorophenyl)sulfonyl](2,4-difluoro-3-{1-[2-(piperidin-1-yl)ethyl]-4-(pyridin-4-yl)-1H-pyrazol-3-yl}phenyl)amino}methyl acetate,
128) {[(2,5-difluorophenyl)sulfonyl](2,4-difluoro-3-{1-[2-(piperidin-1-yl)ethyl]-4-(pyridin-4-yl)-1H-pyrazol-3-yl}phenyl)amino}methyl benzoate,
129) {[(2,5-difluorophenyl)sulfonyl](2,4-difluoro-3-{1-[2-(piperidin-1-yl)ethyl]-4-(pyridin-4-yl)-1H-pyrazol-3-yl}phenyl)amino}methyl N,N-dimethylglycinate and
130) ethyl N-[({[(2,5-difluorophenyl)sulfonyl](2,4-difluoro-3-{1-[2-(piperidin-1-yl)ethyl]-4-(pyridin-4-yl)-1H-pyrazol-3-yl}phenyl)amino}methoxy)carbonyl]-N-methylglycinate.

The present invention also provides a process for the preparation of a compound of formula (I) as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis on non-exemplified compounds according to the invention may be performed by modifications apparent to those skilled in the art, for instance by appropriately protecting interfering groups, by changing to other suitable reagents known in the art, or by making routine modifications of reaction conditions. Alternatively other reactions referred to herein or known in the art will be recognized as having adaptability for preparing other compounds of the invention.

The compounds of formula (I) and the pharmaceutically acceptable salt thereof can be thus prepared according to a process comprising:

a) reacting an optionally protected sulfonamido 3,4-diarylpyrazole compound of formula (II):

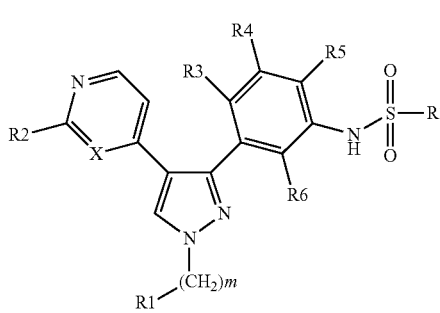

wherein R1, R2, R3, R4, R5, R6, R7, X and m are as defined above, with any suitable agent for inserting on the sulfonamide nitrogen atom the desired R8 group, wherein R8 is as defined above, according to any one of the alternative steps:

a1) with an acyl compound of formula (III):

R27'COW   (III)

wherein W is a suitable leaving group such as hydroxy, halogen or a group OCOR27', wherein R27' is hydrogen or a group optionally substituted selected from straight or branched ($C_1$-$C_8$) alkyl, ($C_2$-$C_8$) alkenyl, ($C_2$-$C_8$) alkynyl, ($C_3$-$C_8$) cycloalkyl, ($C_3$-$C_8$) cycloalkenyl, heterocyclyl, aryl and heteroaryl, to give a compound of formula (I) wherein R8 is COR27, wherein R27 is R27' and R27' is as defined above;

or a2) with an halogenoformate compound of formula (IV):

R30OCO-Hal   (IV)

wherein Hal is halogen and R30 is as defined above, to give a compound of formula (I) wherein R8 is COR27, wherein R27 is OR30 and R30 is as defined above;

or a3) with an alpha-haloalkyl compound of formula (V):

Hal-CHR28OCOR29   (V)

wherein Hal, R28 and R29 are as defined above, to give a compound of formula (I) wherein R8 is CHR28OCOR29, wherein R28 and R29 are as defined above, followed by optional removal of the protecting group, if present;

b) if necessary converting the resultant compound of formula (I):

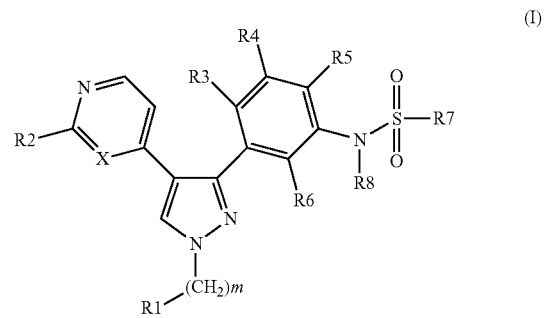

wherein R1, R2, R3, R4, R5, R6, R7, R8, X and m are as defined above, into another compound of formula (I) wherein one or more of R1, R2, R3, R4, R5, R6, R7, X and m is different by known reactions; and/or separating the resultant compound of formula (I) into the single isomers; and/or converting a compound of formula (I) as defined above into a pharmaceutically acceptable salt or converting the salt thereof into the free compound of formula (I) as defined above.

For a reference to any specific compound of formula (I) of the invention, optionally in the form of a pharmaceutically acceptable salt, see the following experimental section.

It is to be noted that the compounds of formula (II) when m is 0 and R1 is hydrogen, when only one of the following tautomeric forms of formula (IIa) or (IIb) is indicated, the remaining one has still to be intended as comprised within the scope of the invention:

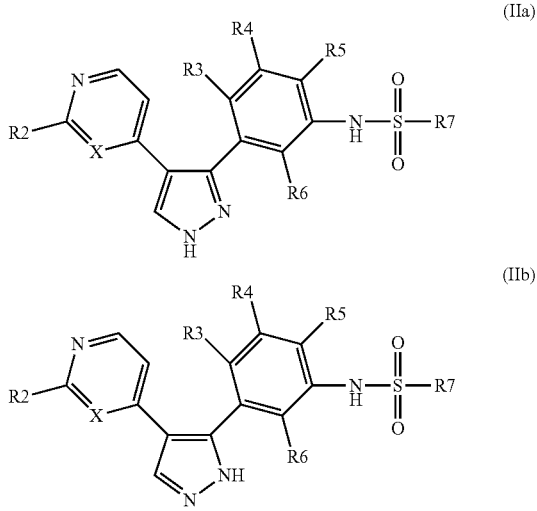

The above processes are analogy processes, which can be carried out according to methods known in the art.

As stated above, it is clear to the person skilled in the art that if a compound of formula (I), prepared according to the above process, is obtained as an admixture of isomers, their separation into the single isomers of formula (I), carried out according to conventional techniques, is still within the scope of the present invention.

According to step (a) of the process, a sulfonamido 3,4-diarylpyrazole compound of formula (II) is reacted, according to well-known methods, with an agent for introducing the desired R8 group.

According to step a1) a compound of formula (I) wherein R8 is an acyl group is prepared. In such a case, the transformation of a compound of formula (II) into a compound of formula (I) is accomplished by reacting the compound of formula (II) with an acyl compound of formula R27'COW, wherein W is a suitable leaving group such as hydroxyl, halogen or an acyloxy group. It is clear to the skilled person that this reaction can be accomplished in a variety of ways and operative conditions, which are widely known in the art for the preparation of carboxamides. As an example, when W is an halogen such as chloride, the reaction is performed in a suitable solvent such as, for instance, dichloromethane, chloroform, tetrahydrofuran, diethyl ether, 1,4-dioxane, acetonitrile, toluene, or N,N-dimethylformamide or the like at a temperature ranging from about −10° C. to reflux and for a suitable time, for instance from about 30 minutes to about 96 hours. The reaction is carried out in the presence of an opportune proton scavenger such as triethylamine, N,N-diisopropylethylamine or pyridine. When W is an hydroxy group, the reaction is carried out in the presence of a coupling agent such as, for instance, 2-(1H-benzotriazol-1-yl)-1,1,3,3-tetramethyluronium tetrafluoroborate (TBTU), 1,3-dicyclohexylcarbodiimide, 1,3-diisopropylcarbodiimide, 1-(3-dimethylaminopropyl)-3-ethylcarbodiimide, N-cyclohexylcarbodiimide-N'-propyloxymethyl polystyrene or N-cyclohexylcarbodiimide-N'-methyl polystyrene, in a suitable solvent such as, for instance, dichloromethane, chloroform, tetrahydrofuran, diethyl ether, 1,4-dioxane, acetonitrile, toluene, or N,N-dimethylformamide at a temperature ranging from about −10° C. to reflux and for a suitable time, for instance from about 30 minutes to about 96 hours. The said reaction is optionally carried out in the presence of a suitable catalyst, for instance 4-dimethylaminopyridine, or in the presence of a further coupling reagent such as N-hydroxybenzotriazole. Alternatively, this same reaction is also carried out, for example, through a mixed anhydride method, by using an alkyl chloroformate such as ethyl, iso-butyl, or iso-propyl chloroformate, in the presence of a tertiary base such as triethylamine, N,N-diisopropylethylamine or pyridine, in a suitable solvent such as, for instance, toluene, dichloromethane, chloroform, tetrahydrofuran, acetonitrile, diethyl ether, 1,4-dioxane, or N,N-dimethylformamide, at a temperature ranging from about −30° C. to room temperature. When W is an acyloxy group of formula OOOR27', the reaction is carried out in the presence of a tertiary base such as triethylamine, N,N-diisopropylethylamine or pyridine, that may be used as the solvent, or in a suitable solvent such as, for instance, toluene, dichloromethane, chloroform, tetrahydrofuran, acetonitrile, diethyl ether, 1,4-dioxane, or N,N-dimethylformamide, at a temperature ranging from about −30° C. to room temperature.

According to step a2) a compound of formula (I) wherein R8 is an alkoxycarbonyl group is prepared. In such a case, the transformation of a compound of formula (II) into a compound of formula (I) is accomplished by reacting the compound of formula (II) with a suitable halogenoformate, also named halogenocarbonate compound of formula R30OCOHal, wherein Hal is a halogen, preferably chlorine. As an example, the reaction is performed in a suitable solvent such as tetrahydrofuran, 1,4-dioxane, dichloromethane, chloroform, acetonitrile, toluene or mixtures thereof, at a temperature ranging from about −5° C. to about 35° C. and for a time varying from about 30 minutes to about 72 hours, in the presence of an opportune proton scavenger such as triethylamine or diisopropylethylamine.

According to step a3) a compound of formula (I) wherein R8 is an alpha-haloalkyl group is prepared. In such a case, the transformation of a compound of formula (II) into a compound of formula (I) is accomplished by reacting the compound of formula (II) with a suitable alpha-haloalkyl compound of formula Hal-CHR28OCOR29, wherein Hal is a halogen, preferably iodine or bromine. As an example, the reaction is performed in a suitable solvent such as tetrahydrofuran, dichloromethane, chloroform, acetonitrile, toluene or mixtures thereof, at a temperature ranging from about −5° C. to about 65° C. and for a time varying from about 30 minutes to about 72 hours, in the presence of an opportune proton scavenger such as triethylamine or diisopropylethylamine.

The strarting material of formula (II) can be prepared as described in the copending patent application WO2010/010154.

The other starting materials of the process of the present invention, i.e. compounds of formula (III), (IV) and (V) comprehensive of any possible variant, as well as any reactant of the process thereof, are known compounds and if not commercially available per se may be prepared as described in the experimental section.

All those with ordinary skills in the art will appreciate that any transformation performed according to said methods may require standard modifications such as, for instance, change to other suitable reagents known in the art, or make routine modifications of reaction conditions.

It is also known to the skilled person that transformation of a chemical function into another may require that one or more reactive centers in the compound containing this function be protected in order to avoid undesired side reactions. Protection of such reactive centers, and subsequent deprotection at the end of the synthetic transformations, can be accomplished following standard procedures described, for instance, in: Green, Theodora W. and Wuts, Peter G. M.—*Protective*

*Groups in Organic Synthesis*, Third Edition, John Wiley & Sons Inc., New York (NY), 1999.

In cases where a compound of formula (I) contains one or more asymmetric centers, said compound can be separated into the single isomers by procedures known to those skilled in the art. Such procedures comprise standard chromatographic techniques, including chromatography using a chiral stationary phase, or crystallization. General methods for separation of compounds containing one or more asymmetric centers are reported, for instance, in Jacques, Jean; Collet, André; Wilen, Samuel H.,—*Enantiomers, Racemates, and Resolutions*, John Wiley & Sons Inc., New York (NY), 1981.

Pharmacology

Assays
In Vitro Cell Proliferation Assay

Exponentially growing human melanoma cells A375 (with a mutated B-RAF) and human melanoma cells Mewo (with wild-type B-Raf) were seeded and incubated at 37° C. in a humidified 5% CO2 atmosphere. After 24 hours, scalar doses of the compound were added to the medium and cells oncubated for 72 hours. At the end of treatment, cells were washed and counted. Cell number was determined by a cellular adenosine triphosphate monitoring system. Cell proliferation was compared to control cells and the concentration inhibiting cell growth by 50% was calculated.

p-MAPK (T2021Y204) ArrayScan Assay

A375 human melanoma cells, having a mutated B-RAF, are seeded in 384-well poly-lysine coated plates (Matrix) at a density of 1000 cells/well with appropriate medium supplemented with 10% FCS and incubated for 16-24 hours. Cells are treated for 1.5 or 2 hours with increasing doses of compounds (starting dose 10 μM, dilution factor 2.5). At the end of the treatment cells are fixed with p-formaldehyde 3.7% for 15-30 min, then I/well) and permeabilized with D-PBS containing washed twice with D-PBS (80 0.1% Triton X-100 and 1% BSA (Sigma-Aldrich) for 15 minutes at room temperature (staining solution). Anti-phospho-MAPK (T202/Y204) monoclonal antibody E10 (Cell Signaling, cat. #9106) diluted 1:100 is added in staining solution and incubated for 1 hour at 37° C. After removal of the primary antibody solution, the anti-mouse Cy™2-conjugated (Green) secondary antibody (Amersham) diluted 1:500 in staining solution containing 2 μg/ml DAPI is added. The plate is incubated for 1 hour at 37° C., washed twice and then red with Cellomics' ArrayScan VTI (4 fields/well, CytoNucTrans algorithm).

The parameter "MEAN_RingAvgIntenCh2", which measures the mean cytoplasmatic fluorescence intensity associated to p-MAPK staining, is reported as the final result.

B-RAF mutations, that constitutively activate the kinase, have been identified in the majority of melanoma and a large fraction of colorectal and papillary thyroid carcinoma. The growth of cells with activated B-RAF strictly depends on B-RAF activity.

Given the above assays, the compounds of formula (I) result to posses a remarkable activity in inhibiting cell proliferation, with $IC_{50}$ values lower than 10 μM on the cell line with mutated B-Raf (A375), and a less potent activity in inhibiting cell proliferation on the cell line with wild-type B-Raf (Mewo), as reported in the following table 1.

In the same table the data obtained with compounds of formula (I) in the ArrayScan assay are also reported and demonstrate the ability of the compounds of formula (I) to inhibit the signal transduction pathway controlled by B-RAF activation in A375 cell line with mutated B-RAF. The $IC_{50}$ values are always lower than 10 μM and are in agreement with the 1050 values obtained in the proliferation assay on the same cell line, confirming that the antiproliferative activity of the compounds is due to the inhibition of B-RAF activity.

TABLE 1

Proliferation and Array Scan data

| Cmpd. No. | Name | Proliferation A375 $IC_{50}$ (μM) | Proliferation Mewo $IC_{50}$ (μM) | Array Scan A375 $IC_{50}$ (μM) |
|---|---|---|---|---|
| 1 | methyl [(2,5-difluorophenyl)sulfonyl]{3-[1-ethyl-4-(pyridin-4-yl)-1H-pyrazol-3-yl]-2,4-difluorophenyl}carbamate | 0.02 | >10 | 0.02 |
| 2 | ethyl [(2,5-difluorophenyl)sulfonyl]{3-[1-ethyl-4-(pyridin-4-yl)-1H-pyrazol-3-yl]-2,4-difluorophenyl}carbamate | 0.37 | >10 | 0.14 |
| 3 | propyl [(2,5-difluorophenyl)sulfonyl]{3-[1-ethyl-4-(pyridin-4-yl)-1H-pyrazol-3-yl]-2,4-difluorophenyl}carbamate | 0.02 | >10 | 0.02 |
| 4 | propan-2-yl [(2,5-difluorophenyl)sulfonyl]{3-[1-ethyl-4-(pyridin-4-yl)-1H-pyrazol-3-yl]-2,4-difluorophenyl}carbamate | 0.02 | >10 | 0.02 |
| 5 | N-[(2,5-difluorophenyl)sulfonyl]-N-{3-[1-ethyl-4-(pyridin-4-yl)-1H-pyrazol-3-yl]-2,4-difluorophenyl}acetamide | 0.02 | >10 | 0.02 |
| 7 | ([(2,5-difluorophenyl)sulfonyl]{3-[1-ethyl-4-(pyridin-4-yl)-1H-pyrazol-3-yl]-2,4-difluorophenyl}amino)methyl acetate | 0.02 | >10 | 0.02 |
| 12 | ethyl [(2,5-difluorophenyl)sulfonyl]{3-[1-methyl-4-(pyridin-4-yl)-1H-pyrazol-3-yl]-2,4-difluorophenyl}carbamate | 0.17 | >10 | 0.02 |
| 45 | N-{3-[4-(2-aminopyridin-4-yl)-1-ethyl-1H-pyrazol-3-yl]-2,4-difluorophenyl}-N-[(2,5-difluorophenyl)sulfonyl]acetamide | 0.09 | >10 | 0.05 |

From all of the above, the novel compounds of formula (I) of the invention appear to be advantageous in the therapy of diseases caused by deregulated protein kinase activity, particularly Raf family kinase activity, such as cancer. Moreover, the compounds of formula (I) of the present invention can be use as prodrugs for releasing the parent drug of formula (II):

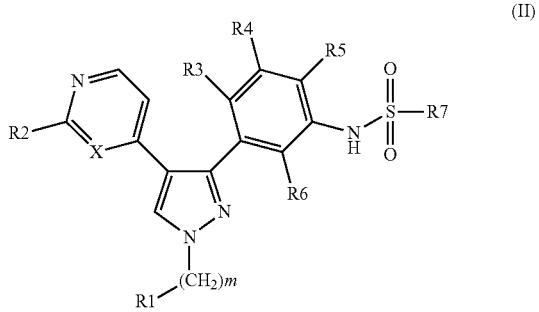

(II)

wherein R1, R2, R3, R4, R5, R6, R7, X and m are as defined above, in vivo.

The released compounds of formula (II) are active as protein kinase inhibitors, particularly as Raf family kinase inhibitors. In therapy, they may be used in the treatment of diseases caused by deregulated protein kinase activity such as cancer.

Typically, the group R8 as defined above is the prodrug modification group, also referred to as promoiety.

Said prodrug modification group is wholly or partially cleaved by degradative enzymes. A variety of degradative enzymes may chemically alter the prodrug modification group to form the parent kinase inhibitor. Examples of such enzymes include, but are not limited to, proteases, peptidases, amidases, esterases, glucoronidases, hydrolases and others.

In Vitro Conversion of a Prodrug of Formula (I) into the Parent Compound of Formula (II)

A compound of formula (I) of the present invention, dissolved in DMSO, was incubated at 37° C. in PBS at pH 7.4 or fresh mouse plasma. Aliquots were withdrawn and analysed by HPLC/MS at 0, 5, 15, 60 and 120 minutes. The UV signal in the range 210-400 nm was used for the quantification of the chromatographic peaks either of the compound of formula (I) and the parent compound of formula (II).

FIG. 1 shows the stability of Cmpd. No. 2, taken as a representative of the compounds of formula (I) of the present invention, in PBS buffer, demonstrating that Cmpd. No. 2 is stable in buffer and not converted in the corresponding parent compound.

Figure 2:
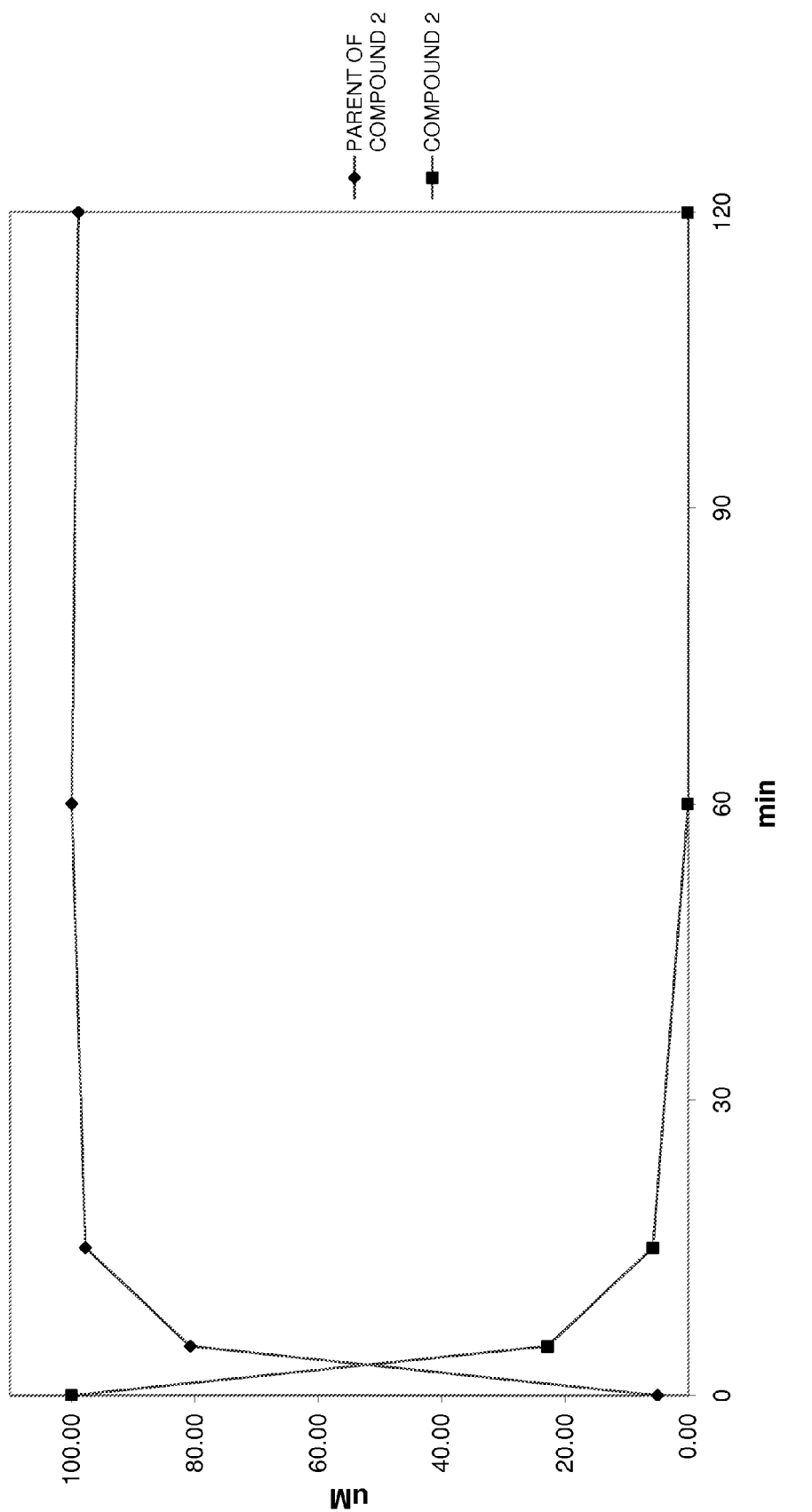
FIG. 2 refers to the stability study in plasma and shows the conversion in fresh mouse plasma of Compound No. 2, taken as a representative of the compounds of formula (I) of the present invention, into the parent of Compound No. 2.

FIG. 2 shows the conversion in fresh mouse plasma of Cmpd. No. 2, taken as a representative of the compounds of formula (I) of the present invention, into the parent of Cpmd. No. 2, demonstrating that Cmpd. No. 2 is rapidly converted into the corresponding parent compound when incubated with plasma.

Bioavailability Assay

In addition to in vitro methods, in vivo methods, such as pharmacokinetic studies, can be performed in a range of animals. A compound of formula (I) of the present invention can be administered to animals, for instance mouse or rat, at different dosages, and by different route of administration, preferably per os. Blood samples can be collected at serial time points and the samples assayed for the presence of the parent compound of formula II.

A compounds of formula (I) of the present invention, formulated in 0.5% Methocel®, was administered orally to mice (10 to 100 mg/Kg) in pharmacokinetic studies and its conversion into the corresponding parent compound (II) as defined above was monitored in blood by HPLC/MS analysis at 15 and 30 min, 1, 6 and 24 h post-dosing. All blood samples were taken from saphenous vein.

Oral bioavailability (Fos) was calculated as percent ratio of average oral AUC value of parent compound after prodrug to average IV AUC value of parent compound after prodrug following parent compound dose normalization.

The following table 2 reports oral bioavailability (Fos) of the parent of Cmpd. No. 2 and of the parent of Cmpd. No. 45, after administration of theirs respective prodrugs taken as representatives of the compounds of formula (I) of the present invention.

TABLE 2

| | Bioavailability in mice | |
|---|---|---|
| Cmpd. No. | Parent Compound Name | Fos (mouse) |
| 2 | N-[2,4-Difluoro-3-(1-ethyl-4-(pyridin-4-yl)-1H-pyrazol-3-yl)-phenyl]-2,5-difluoro-benzenesulfonamide | 44.4 |
| 45 | N-{3-[4-(2-aminopyridin-4-yl)-1-ethyl-1H-pyrazol-3-yl]-2,4-difluorophenyl}-2,5-difluorobenzenesulfonamide | 39.4 |

From all of the above, the compounds of formula (I) of the invention appear to be endowed with a biological profile, considered as a whole, which is unexpectedly superior to that of the prior art and, hence, are particularly advantageous, in therapy, against proliferative disorders associated with an altered kinase activity, particularly Raf family kinase activity, such as cancer.

The compounds of the present invention can be administered either as single agents or, alternatively, in combination with known anticancer treatments such as radiation therapy or chemotherapy regimen in combination with, for example, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

If formulated as a fixed dose, such combination products employ the compounds of this invention within the dosage range described below and the other pharmaceutically active agent within the approved dosage range. Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, and conditions of the patient and administration route.

For example, a suitable dosage adopted for oral administration of a compound of formula (I) may range from about 10 to about 1 g per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions.

As an example the syrups may contain, as a carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

Experimental Section

For a reference to any specific compound of formula (I) of the invention, optionally in the form of a pharmaceutically acceptable salt, see the experimental section and claims. Referring to the examples that follow, compounds of the present invention were synthesized using the methods described herein, or other methods, which are well known in the art.

The short forms and abbreviations used herein have the following meaning:

| | |
|---|---|
| g (grams) | mg (milligrams) |
| ml (milliliters) | mM (millimolar) |
| μM (micromolar) | mmol (millimoles) |
| h (hours) | MHz (Mega-Hertz) |
| mm (millimetres) | Hz (Hertz) |
| M (molar) | min (minutes) |
| mol (moles) | TLC (thin layer chromatography) |
| r.t. (room temperature) | |
| TFA (trifluoroacetic acid) | TEA (triethylamine) |
| DIPEA (N,N-diisopropyl-N-ethylamine) | DMF (N,N-dimethyl formamide) |
| THF (tetrahydrofuran) | DCM (dichloromethane) |
| MeOH (Methanol) | Hex (hexane) |
| TIPS (triisopropylsilyl) | DMSO (dimethylsulfoxide) |

-continued

| | |
|---|---|
| TBDMS (dimethyl-tert-butylsilyl) | bs (broad singlet) |
| BOC (tert-butyloxycarbonyl) | Ac (acetyl) |
| NaH = sodium hydride, 60% in mineral oil | $Ac_2O$ acetic anhydride |
| | ESI = electrospray ionization |
| TBTU (2-(1H-benzotriazol-1-yl)-1,1,3,3-tetramethyluronium tetrafluoroborate | |
| RP-HPLC (reverse phase high performance liquid chromatography) | |
| PBS = Phosphate Buffered Saline | |
| AUC = Area Under the Curve | |

With the aim to better illustrate the present invention, without posing any limitation to it, the following examples are now given.

As used herein the symbols and conventions used in the processes, schemes and examples are consistent with those used in the contemporary scientific literature, for example, the *Journal of the American Chemical Society* or the *Journal of Biological Chemistry*.

Unless otherwise noted, all materials were obtained from commercial suppliers, of the best grade and used without further purification. Anhydrous solvent such as DMF, THF, $CH_2Cl_2$ and toluene were obtained from the Aldrich Chemical Company. All reactions involving air- or moisture-sensitive compounds were performed under nitrogen or argon atmosphere.

General Purification and Analytical Methods

Flash Chromatography was performed on silica gel (Merck grade 9395, 60A). HPLC was performed on Waters X Terra RP 18 (4.6×50 mm, 3.5 μm) column using a Waters 2790 HPLC system equipped with a 996 Waters PDA detector and Micromass mod. ZQ single quadrupole mass spectrometer, equipped with an electrospray (ESI) ion source. Mobile phase A was ammonium acetate 5 mM buffer (pH 5.5 with acetic acid-acetonitrile 95:5), and Mobile phase B was water-acetonitrile (5:95). Gradient from 10 to 90% B in 8 minutes, hold 90% B 2 minutes. UV detection at 220 nm and 254 nm. Flow rate 1 ml/min. Injection volume 10 microL. Full scan, mass range from 100 to 800 amu. Capillary voltage was 2.5 KV; source temperature was 120° C.; cone was 10 V. Retention times (HPLC r.t.) are given in minutes at 220 nm or at 254 nm. Mass are given as m/z ratio.

When necessary, compounds were purified by preparative HPLC on a Waters Symmetry C18 (19×50 mm, 5 um) column or on a Waters X Terra RP 18 (30×150 mm, 5 μm) column using a Waters preparative HPLC 600 equipped with a 996 Waters PDA detector and a Micromass mod. ZMD single quadrupole mass spectrometer, electron spray ionization, positive mode. Mobile phase A was water-0.01% trifluoroacetic acid, and mobile phase B was acetonitrile. Gradient from 10 to 90% B in 8 min, hold 90% B 2 min. Flow rate 20 mL/min. In alternative, mobile phase A was water-0.1% $NH_3$, and mobile phase B was acetonitrile. Gradient from 10 to 100% B in 8 min, hold 100% B 2 min. Flow rate 20 mL/min.

1H-NMR spectrometry was performed on a Mercury VX 400 operating at 400.45 MHz equipped with a 5 mm double resonance probe [1H (15N-31P) ID_PFG Varian].

The following examples are intended to illustrate but not in any way limit the invention. While the invention has been described with reference to specific methods and embodiments, it will be appreciated that various modifications may be made without departing from the invention.

Example 1 methyl [(2,5-difluorophenyl)sulfonyl]{3-[1-ethyl-4-(pyridin-4-yl)-1H-pyrazol-3-yl]-2,4-difluorophenyl}carbamate (Cmpd No. 1)

(I), R1, R2, R4, R5=H, R3, R6=F, R7=2,5-difluorophenyl, R8=COOCH₃, X=CH, m=2

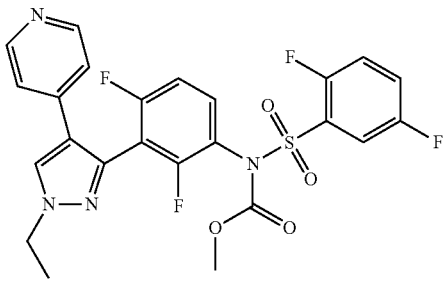 [SMILES: CCn1cc(-c2ccncc2)c(-c2c(F)ccc(N(C(=O)OC)S(=O)(=O)c3cc(F)ccc3F)c2F)n1]

N-{2,4-difluoro-3-[1-ethyl-4-(pyridin-4-yl)-1H-pyrazol-3-yl]phenyl}-2,5-difluorobenzenesulfonamide (80 mg, 0.168 mmol) was suspended in 3.5 mL of DCM and TEA (18.7 mg, 25.8 μL, 0.185 mmol) was added. Methyl chloroformate (17.5 mg, 13.0 L, 0.185 mmol) was added to the solution so obtained, and the reaction mixture was stirred at room temperature for 3 hours, diluted with DCM, and poured in water. The organic layer was washed three times with water, once with brine, dried over Na₂SO₄ and concentrated to dryness. The solid so obtained was taken up with ethyl ether and filtered (72 mg, 80% yield)

¹H NMR (401 MHz, DMSO-d₆) δ=8.53 (s, 1H), 8.40-8.45 (m, 2H), 7.74-7.87 (m, 3H), 7.62 (td, J=4.1, 9.5 Hz, 1H), 7.41 (td, J=1.3, 9.0 Hz, 1H), 7.10-7.17 (m, 2H), 4.27 (q, J=7.3 Hz, 2H), 3.65 (s, 3H), 1.49 (t, J=7.3 Hz, 3H)

HRMS (ESI) calcd for C₂₄H₁₈F₄N₄O₄S [M+H]⁺ 535.1058. found 535.1044.

Operating in an analogous way the following compounds were obtained:

ethyl [(2,5-difluorophenyl)sulfonyl]{3-[1-ethyl-4-(pyridin-4-yl)-1H-pyrazol-3-yl]-2,4-difluorophenyl}carbamate (Cmpd No. 2)

(I), R1, R2, R4, R5=H, R3, R6=F, R7=2,5-difluorophenyl, R8=COOCH₂CH₃, X=CH, m=2

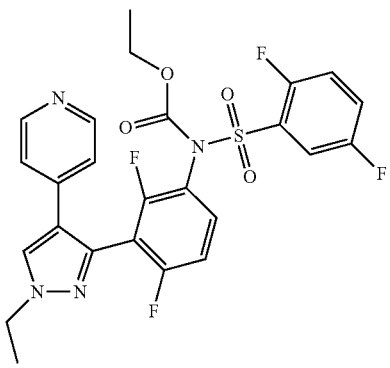 [SMILES: CCOC(=O)N(c1ccc(F)c(-c2nn(CC)cc2-c2ccncc2)c1F)S(=O)(=O)c1cc(F)ccc1F]

The solid obtained was suspended in 1,4-dioxane and a solution of 25% HCl in water (1.1 eq.) was added. The solution was evaporated to dryness to yield the target compound as the corresponding hydrochloride salt. (Yield 89%)

¹H NMR (401 MHz, DMSO-d₆) δ=8.88 (s, 1H), 8.61-8.73 (m, 2H), 7.75-7.90 (m, 3H), 7.59-7.69 (m, 3H), 7.42-7.54 (m, 1H), 4.33 (q, J=7.3 Hz, 2H), 4.06-4.16 (q, J=7.1 Hz, 2H), 1.51 (t, J=7.3 Hz, 3H), 1.02 (t, J=7.1 Hz, 3H)

HRMS (ESI) calcd for C₂₅H₂₀F₄N₄O₄S [M+H]⁺ 549.1214. found 549.1218.

propyl [(2,5-difluorophenyl)sulfonyl]{3-[1-ethyl-4-(pyridin-4-yl)-1H-pyrazol-3-yl]-2,4-difluorophenyl}carbamate (Cmpd No. 3)

(I), R1, R2, R4, R5=H, R3, R6=F, R7=2,5-difluorophenyl, R8=COOCH₂CH₂CH₃, X=CH, m=2

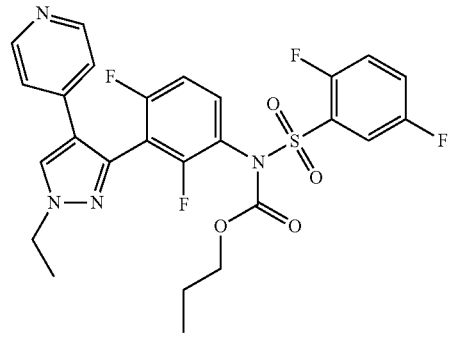 [SMILES: CCCOC(=O)N(c1ccc(F)c(-c2nn(CC)cc2-c2ccncc2)c1F)S(=O)(=O)c1cc(F)ccc1F]

(Yield 77%)

¹H NMR (401 MHz, DMSO-d₆) δ=8.53 (s, 1H), 8.38-8.45 (m, 2H), 7.80-7.87 (m, 1H), 7.73-7.80 (m, 2H), 7.62 (td, J=4.0, 9.4 Hz, 1H), 7.41 (td, J=1.5, 8.9 Hz, 1H), 7.10-7.16 (m, 2H), 4.21-4.33 (m, 2H), 3.98-4.09 (m, 2H), 1.48 (t, J=7.3 Hz, 3H), 1.35-1.46 (m, 2H), 0.65 (t, J=7.4 Hz, 3H)

HRMS (ESI) calcd for C₂₆H₂₂F₄N₄O₄S [M+H]⁺ 563.1371. found 563.1364.

propan-2-yl [(2,5-difluorophenyl)sulfonyl]{3-[1-ethyl-4-(pyridin-4-yl)-1H-pyrazol-3-yl]-2,4-difluorophenyl}carbamate ((Cmpd No. 4)

(I), R1, R2, R4, R5=H, R3, R6=F, R7=2,5-difluorophenyl, R8=COOCH₂(CH₃)₂, X=CH, m=2

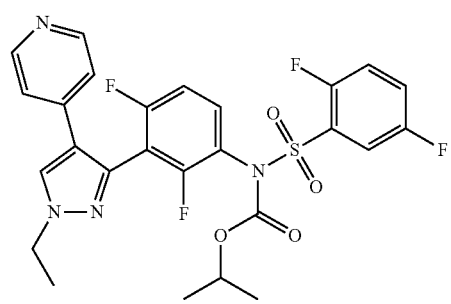 [SMILES: CCn1cc(-c2ccncc2)c(-c2c(F)ccc(N(C(=O)OC(C)C)S(=O)(=O)c3cc(F)ccc3F)c2F)n1]

(Yield 99%)

¹H NMR (401 MHz, DMSO-d₆) δ=8.53 (s, 1H), 8.35-8.44 (m, 2H), 7.80-7.89 (m, 1H), 7.72-7.80 (m, 2H), 7.63 (td, J=4.1, 9.4 Hz, 1H), 7.40 (td, J=1.6, 8.8 Hz, 1H), 7.06-7.19 (m,

2H), 4.84 (quin, J=6.2 Hz, 1H), 4.27 (q, J=7.3 Hz, 2H), 1.48 (t, J=7.3 Hz, 3H), 0.83-1.16 (m, J=6.1 Hz, 6H).

HRMS (ESI) calcd for $C_{26}H_{22}F_4N_4O_4S$ $[M+H]^+$ 563.1371. found 563.1372.

ethyl [(2,5-difluorophenyl)sulfonyl]{3-[1-ethyl-4-(pyridin-4-yl)-1H-pyrazol-3-yl]-2-methylphenyl}carbamate (Cmpd No. 72)

(I), R1, R2, R3, R4, R5=H, R6=methyl, R7=2,5-difluorophenyl, R8=COOCH$_2$CH$_3$, X=CH, m=2

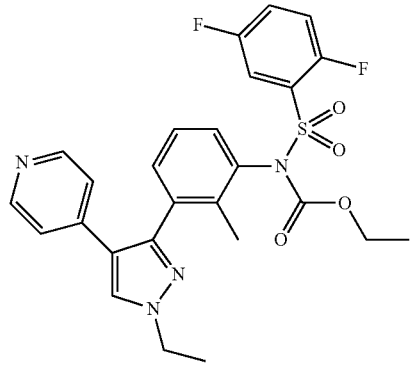 [SMILES: CCOC(=O)N(c1cccc(-c2nn(CC)cc2-c2ccncc2)c1C)S(=O)(=O)c1cc(F)ccc1F]

$^1$H NMR (401 MHz, DMSO-d$_6$) δ=8.50 (s, 1H), 8.29-8.35 (m, 2H), 7.75-7.90 (m, 2H), 7.66 (td, J=4.0, 9.5 Hz, 1H), 7.35-7.48 (m, 3H), 7.03-7.07 (m, 2H), 4.24 (q, J=7.3 Hz, 2H), 3.99-4.17 (m, 2H), 1.95 (s, 3H), 1.49 (t, J=7.3 Hz, 3H), 1.00 (t, J=7.1 Hz, 3H)

HRMS (ESI) calcd for $C_{26}H_{24}F_2N_4O_4S$ $[M+H]^+$ 527.1559. found 527.1546.

propyl [(2,5-difluorophenyl)sulfonyl]{3-[1-ethyl-4-(pyridin-4-yl)-1H-pyrazol-3-yl]-2-methylphenyl}carbamate (Cmpd No. 73)

(I), R1, R2, R3, R4, R5=H, R6=methyl, R7=2,5-difluorophenyl, R8=COOCH$_2$CH$_2$CH$_3$, X=CH, m=2

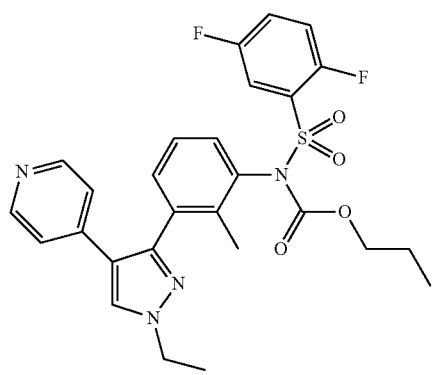 [SMILES: CCCOC(=O)N(c1cccc(-c2nn(CC)cc2-c2ccncc2)c1C)S(=O)(=O)c1cc(F)ccc1F]

$^1$H NMR (401 MHz, DMSO-d$_6$) δ=8.49 (s, 1H), 8.30-8.33 (m, 2H), 7.75-7.88 (m, 2H), 7.67 (td, J=4.0, 9.5 Hz, 1H), 7.35-7.48 (m, 3H), 7.04-7.08 (m, 2H), 4.19-4.28 (m, 2H), 3.95-4.10 (m, 2H), 1.98 (s, 3H), 1.48 (t, J=7.3 Hz, 3H), 1.33-1.45 (m, 2H), 0.66 (t, J=7.4 Hz, 3H)

HRMS (ESI) calcd for $C_{27}H_{26}F_2N_4O_4S$ $[M+H]^+$ 541.1716. found 541.1691.

ethyl [(2,5-difluorophenyl)sulfonyl]{3-[1-methyl-4-(pyridin-4-yl)-1H-pyrazol-3-yl]-2,4-difluorophenyl}carbamate (Cmpd No. 74)

(I), R1, R2, R4, R5=H, R3, R6=F, R7=2,5-difluorophenyl, R8=COOCH$_2$CH$_3$, X=CH, m=1

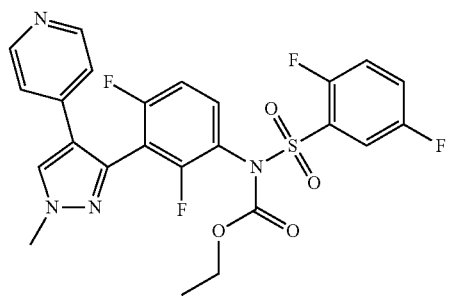 [SMILES: CCOC(=O)N(c1ccc(F)c(-c2nn(C)cc2-c2ccncc2)c1F)S(=O)(=O)c1cc(F)ccc1F]

$^1$H NMR (401 MHz, DMSO-d$_6$) δ=8.47 (s, 1H), 8.39-8.43 (m, 2H), 7.80-7.87 (m, 1H), 7.72-7.80 (m, 2H), 7.62 (td, J=4.1, 9.4 Hz, 1H), 7.41 (td, J=1.6, 8.8 Hz, 1H), 7.09-7.15 (m, 2H), 4.06-4.17 (m, 2H), 3.99 (s, 3H), 1.00 (t, J=7.1 Hz, 3H)

HRMS (ESI) calcd for $C_{24}H_{18}F_4N_4O_4S$ $[M+H]^+$ 535.1058. found 535.1052.

Example 2

N-[(2,5-difluorophenyl)sulfonyl]-N-{3-[1-ethyl-4-(pyridin-4-yl)-1H-pyrazol-3-yl]-2,4-difluorophenyl}acetamide (Cmpd No. 5)

(I), R1, R2, R4, R5=H, R3, R6=F, R7=2,5-difluorophenyl, R8=COCH$_3$, X=CH, m=2

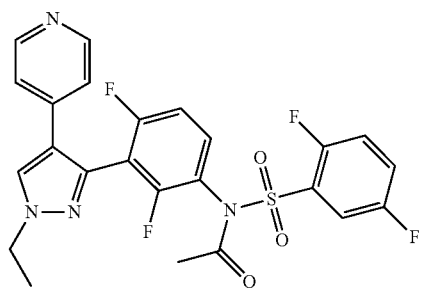 [SMILES: CCn1cc(-c2ccncc2)c(-c2c(F)ccc(N(C(C)=O)S(=O)(=O)c3cc(F)ccc3F)c2F)n1]

N-{2,4-difluoro-3-[1-ethyl-4-(pyridin-4-yl)-1H-pyrazol-3-yl]phenyl}-2,5-difluorobenzenesulfonamide (80 mg, 0.168 mmol) was suspended in 3.5 mL of DCM and TEA (18.7 mg, 25.8 µL, 0.185 mmol) was added. Acetyl chloride (20.0 mg, 18.0 µL, 0.252 mmol) was added to the solution so obtained, and the reaction mixture was stirred at room temperature overnight, diluted with DCM, and poured in water. The organic layer was washed three times with water, once with brine, dried over Na$_2$SO$_4$ and concentrated to dryness. The solid so obtained was taken up with ethyl ether and filtered (79 mg, 91% yield)

$^1$H NMR (401 MHz, DMSO-d$_6$) δ=8.52 (s, 1H), 8.40-8.43 (m, 2H), 7.83-7.91 (m, 1H), 7.71-7.83 (m, 2H), 7.60 (td,

J=4.0, 9.5 Hz, 1H), 7.40-7.53 (m, 2H), 7.12-7.19 (m, 2H), 4.28 (q, J=7.3 Hz, 2H), 1.96 (s, 3H), 1.49 (t, J=7.3 Hz, 3H)

HRMS (ESI) calcd for $C_{24}H_{18}F_4N_4O_3S$ [M+H]$^+$ 519.1109. found 519.1094.

Operating in an analogous way the following compounds were obtained:

N-{3-[4-(2-aminopyridin-4-yl)-1-ethyl-1H-pyrazol-3-yl]-2,4-difluorophenyl}-N-[(2,5-difluorophenyl)sulfonyl]acetamide (Cmpd No. 45)

(I), R1, R4, R5=H, R2=NH2, R3, R6=F,
R7=2,5-difluorophenyl, R8=COCH$_3$, X=CH, m=2

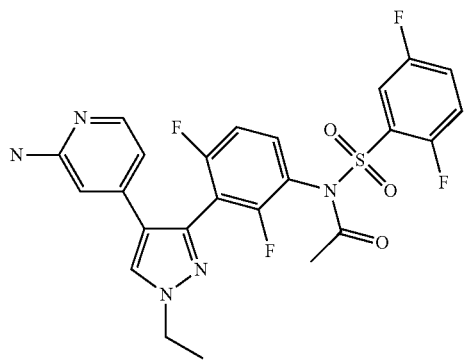 [SMILES: CCn1cc(-c2ccnc(N)c2)c(-c2c(F)ccc(N(C(C)=O)S(=O)(=O)c3cc(F)ccc3F)c2F)n1]

The solid was purified by flash chromatography on silica gel (DCM/MeOH 96:4). Yield 70%

$^1$H NMR (401 MHz, DMSO-d$_6$) δ=8.29 (s, 1H), 7.74-7.90 (m, 3H), 7.73-7.75 (m, 1H), 7.60 (td, J=4.2, 9.5 Hz, 1H), 7.42-7.49 (m, 1H), 6.26 (dd, J=1.6, 5.4 Hz, 1H), 6.22 (s, 1H), 5.73 (br. s, 2H), 4.21-4.30 (q, 2H), 1.91 (s, 3H), 1.44-1.50 (m, 3H)

HRMS (ESI) calcd for $C_{24}H_{19}F_4N_5O_3S$ [M+H]$^+$ 534.1218. found 534.1223.

Example 3 ethyl N-{[([(2,5-difluorophenyl)sulfonyl]{3-[1-ethyl-4-(pyridin-4-yl)-1H-pyrazol-3-yl]-2,4-difluorophenyl}amino)methoxy]carbonyl}-N-methylglycinate (Cmpd No. 10)

(I), R1, R2, R4, R5=H, R3, R6=F, R7=2,5-difluorophenyl, R8=CH$_2$OCON(CH$_3$)CH$_2$COOCH$_2$CH$_3$, X=CH, m=2

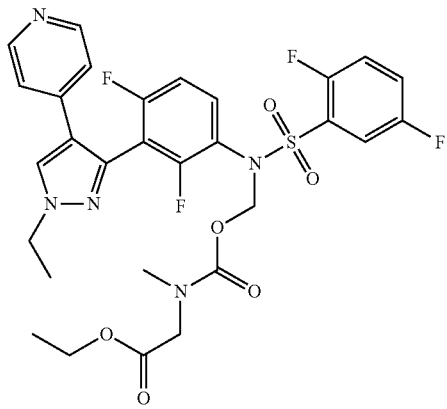 [SMILES: CCOC(=O)CN(C)C(=O)OCN(c1ccc(F)c(-c2nn(CC)cc2-c2ccncc2)c1F)S(=O)(=O)c1cc(F)ccc1F]

ethyl N-[(chloromethoxy)carbonyl]-N-methylglycinate

Sarcosine hydrochloride (426 mg, 2.772 mmol) was suspended in 6.0 mL of DCM and TEA (560 mg, 770 μL, 5.544 mmol) was added. Chloromethyl chloroformate (325 mg, 224 μL, 2.52 mmol) was added, and the reaction mixture was stirred at room temperature overnight. The suspension was diluted with DCM, and poured in water. The organic layer was washed once with water, once with brine, dried over Na$_2$SO$_4$ and concentrated to dryness. The oily material so obtained was monitored by $^1$H NMR and used for the next step.

$^1$H NMR (300 MHz, CDCl$_3$) δ=5.79 and 5.76 (2s, 2H, tautomers), 4.22 (q, 2H), 4.05 and 3.99 (2s, 2H, tautomers), 3.03 and 3.01 (2s, 3H, tautomers), 1.28 (t, 3H).

ethyl N-[(iodomethoxy)carbonyl]-N-methylglycinate ethyl N-[(chloromethoxy)carbonyl]-N-methylglycinate obtained in the previous step was dissolved in acetone (5.0 mL). Sodium iodide (755 mg, 5.04 mmol) was added, and the reaction mixture was stirred at room temperature overnight. The solvent was evaporated to dryness, the crude re-suspended in DCM and poured in water. The organic layer was washed once with water, once with brine, dried over Na$_2$SO$_4$ and concentrated to dryness.

The reddish oily material so obtained (303 mg) was monitored by $^1$H NMR and used for the next step.

$^1$H NMR (300 MHz, CDCl$_3$) δ=6.02 and 5.99 (2s, 2H, tautomers), 4.22 (q, 2H), 4.04 and 3.95 (2s, 2H, tautomers), 3.01 and 2.98 (2s, 3H, tautomers), 1.29 (t, 3H).

N-{2,4-difluoro-3-[1-ethyl-4-(pyridin-4-yl)-1H-pyrazol-3-yl]phenyl}-2,5-difluorobenzenesulfonamide (80 mg, 0.168 mmol) was suspended in 3.5 mL of DCM and TEA (18.7 mg, 25.8 μL, 0.185 mmol) was added. Ethyl N—[(iodomethoxy)carbonyl]-N-methylglycinate obtained in the previous step was added portion-wise. After stirring at room temperature for 48 hours, the reaction mixture was diluted with DCM, and poured in water. The organic layer was washed three times with water, once with brine, dried over Na$_2$SO$_4$ and concentrated to dryness. The solid was purified by flash chromatography on silica gel (DCM/MeOH 97:3). Yield 23%

$^1$H NMR (401 MHz, DMSO-d$_6$) δ=8.95-8.99 (m, 1H), 8.91 (d, J=7.1 Hz, 2H), 7.77 (dd, J=1.9, 7.0 Hz, 2H), 7.38-7.64 (m, 4H), 7.22-7.32 (m, 1H), 6.29 and 6.25 (2 s, 2H, tautomers), 4.30 (q, J=7.2 Hz, 2H), 4.13 and 4.02 (2s, 2H, tautomers), 4.03-4.12 (m, 2H), 1.48 (t, J=7.3 Hz, 3H), 1.14 (t, J=7.1 Hz, 3H)

HRMS (ESI) calcd for $C_{29}H_{27}F_4N_5O_6S$ [M+H]$^+$ 650.1691. found 650.1669.

Operating in an analogous way the following compounds were obtained:

([(2,5-difluorophenyl)sulfonyl]{3-[1-ethyl-4-(pyridin-4-yl)-1H-pyrazol-3-yl]-2,4-difluorophenyl}amino)methyl acetate (Cmpd No. 7)

(I), R1, R2, R4, R5=H, R3, R6=F,
R7=2,5-difluorophenyl, R8=CH$_2$OCOCH$_3$, X=CH,
m=2

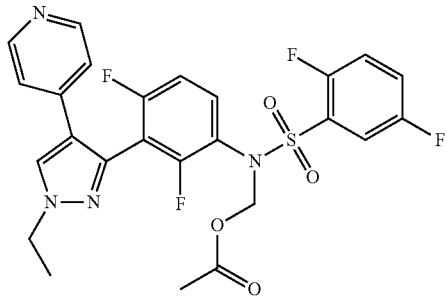 [SMILES: CCn1cc(-c2ccncc2)c(-c2c(F)ccc(N(COC(C)=O)S(=O)(=O)c3cc(F)ccc3F)c2F)n1]

The solid was purified by flash chromatography on silica gel (Hexane/Ethyl Acetate 3:7). Yield 72%

$^1$H NMR (401 MHz, DMSO-d$_6$) δ=8.49 (s, 1H), 8.37-8.44 (m, 2H), 7.61-7.72 (m, 1H), 7.52-7.61 (m, 2H), 7.43-7.52 (m, 1H), 7.26 (td, J=1.5, 8.8 Hz, 1H), 7.05-7.10 (m, 2H), 5.65 (s, 2H), 4.24 (q, J=7.2 Hz, 2H), 1.94 (s, 3H), 1.43-1.49 (m, 3H)

HRMS (ESI) calcd for C$_{25}$H$_{20}$F$_4$N$_4$O$_4$S [M+H]$^+$ 549.1214. found 549.1207.

The invention claimed is:

1. A compound of the formula (I)

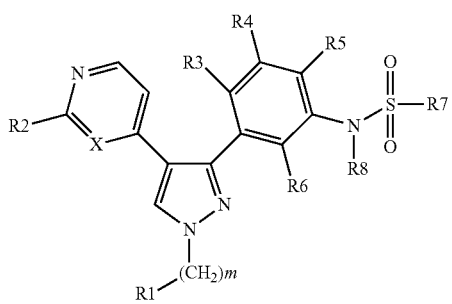

wherein:
m is an integer from 0 to 6;
R1 is hydrogen, trichloromethyl, trifluoromethyl, halogen, cyano, NR10R11, or straight or branched (C$_1$-C$_8$) alkyl, wherein:
R10 and R11, taken together with the atoms to which they are bonded form a heterocyclyl optionally containing one additional heteroatom or heteroatomic group selected from S, O, N and NH;
X is —CH or N;
R2 is hydrogen, halogen, or NR17R18, wherein:
R17 and R18 are, each independently one from the other, hydrogen or a straight or branched (C$_1$-C$_8$) alkyl optionally substituted with alkoxycarbonylamino;
R3, R4, R5 and R6 are, each independently one from the other, hydrogen, halogen, trifluoromethyl, trichloromethyl, cyano, or a group selected from straight or branched (C$_1$-C$_8$) alkyl and (C$_3$-C$_8$) cycloalkyl, R7 is selected from straight or branched (C$_1$-C$_8$) alkyl, (C$_3$-C$_8$) cycloalkyl, and phenyl, wherein R7 is optionally substituted with one or more substituents selected from halogen, (C$_1$-C$_8$) alkyl, trifluoromethyl, and cyano;
R8 is COR27 or CHR28OCOR29, wherein:
R27 is straight or branched (C$_1$-C$_8$) alkyl or a group OR30, wherein the (C$_1$-C$_8$) alkyl is optionally substituted with dialkylamino:
R30 is straight or branched (C$_1$-C$_8$) alkyl;
R28 is hydrogen;
R29 is straight or branched (C$_1$-C$_8$) alkyl, NR31R32, or phenyl, wherein the (C$_1$-C$_8$) alkyl is optionally substituted with dialkylamino, wherein:
R31 and R32 are, each independently one from the other, straight or branched (C$_1$-C$_8$) alkyl optionally substituted with alkoxycarbonyl;
or a pharmaceutically acceptable salt thereof.

2. A compound of claim 1, or a pharmaceutically acceptable salt thereof, wherein m is 1 or 2.

3. A compound of claim 2, or a pharmaceutically acceptable salt thereof, wherein:
R10 and R11 taken together with the atoms to which they are bonded form a heterocyclyl;
R3, R4, R5 and R6 are, each independently one from the other, hydrogen, halogen, trifluoromethyl, trichloromethyl, or straight or branched (C$_1$-C$_8$) alkyl; and
R7 is phenyl optionally substituted with one or more substituents selected from halogen, (C$_1$-C$_8$) alkyl, trifluoromethyl, and cyano.

4. A compound of claim 3, or a pharmaceutically acceptable salt thereof, wherein:
R7 is phenyl optionally substituted with one or more halogen;
R27 is straight or branched (C$_1$-C$_8$) alkyl or OR30, wherein the (C$_1$-C$_8$) alkyl is optionally substituted with —NMe$_2$;
R29 is straight or branched (C$_1$-C$_8$) alkyl, NR31R32, or phenyl, wherein the (C$_1$-C$_8$) alkyl is optionally substituted with —NMe$_2$; and
R31 and R32 are, each independently one from the other, straight or branched (C$_1$-C$_8$) alkyl optionally substituted with CO$_2$Et.

5. A compound of claim 4, or a pharmaceutically acceptable salt thereof, wherein:
R2 is hydrogen or NR17R18, wherein R17 and R18 are, each hydrogen; and
R3, R4, R5 and R6 are, each independently one from the other, hydrogen, halogen, or straight or branched (C$_1$-C$_8$) alkyl.

6. A compound of claim 5, or a pharmaceutically acceptable salt thereof, wherein:
R1 is hydrogen, halogen, or NR10R11.

7. A compound of claim 6, or a pharmaceutically acceptable salt thereof, wherein:
R10 and R11 taken together with the atoms to which they are bonded form a piperidinyl;
R7 is phenyl optionally substituted with one or more fluoro;
R27 is methyl, optionally substituted with —NMe$_2$; or OR30;
R29 is methyl optionally substituted with —NMe$_2$; NR31R32; or phenyl; and
R31 and R32 are, each independently one from the other, methyl optionally substituted with CO$_2$Et.

8. A compound of claim 1, or a pharmaceutically acceptable salt thereof, selected from the group consisting of:

methyl [(2,5-difluorophenyl)sulfonyl]{3-[1-ethyl-4-(pyridin-4-yl)-1H-pyrazol-3-yl]-2,4-difluorophenyl}carbamate,
ethyl [(2,5-difluorophenyl)sulfonyl]{3-[1-ethyl-4-(pyridin-4-yl)-1H-pyrazol-3-yl]-2,4-difluorophenyl}carbamate,
propyl [(2,5-difluorophenyl)sulfonyl]{3-[1-ethyl-4-(pyridin-4-yl)-1H-pyrazol-3-yl]-2,4-difluorophenyl) carbamate,
propan-2-yl [(2,5-difluorophenyl)sulfonyl]{3-[1-ethyl-4-(pyridin-4-yl)-1H-pyrazol-3-yl]-2,4-difluorophenyl}carbamate,
N-[(2,5-difluorophenyl)sulfonyl]-N-(3-[1-ethyl-4-(pyridin-4-yl)-1H-pyrazol-3-yl]-2,4-difluorophenyl}acetamide,
N-[(2,5-difluorophenyl)sulfonyl]-N-{3-[1-ethyl-4-(pyridin-4-yl)-1H-pyrazol-3-yl]-2,4-difluorophenyl}-N2,N2-dimethylglycinamide,
([(2,5-difluorophenyl)sulfonyl]{3-[1-ethyl-4-(pyridin-4-yl)-1H-pyrazol-3-yl]-2,4-difluorophenyl}amino)methyl acetate,
([(2,5-difluorophenyl)sulfonyl]{3-[1-ethyl-4-(pyridin-4-yl)-1H-pyrazol-3-yl]-2,4-difluorophenyl}amino)methyl benzoate,
([(2,5-difluorophenyl)sulfonyl]{3-[1-ethyl-4-(pyridin-4-yl)-1H-pyrazol-3-yl]-2,4-difluorophenyl}amino)methyl N,N-dimethylglycinate,
ethyl N-{[([(2,5-difluorophenyl)sulfonyl]{3-[1-ethyl-4-(pyridin-4-yl)-1H-pyrazol-3-yl]-2,4-difluorophenyl}amino) methoxy]carbonyl}-N-methylglycinate,
methyl [(2,5-difluorophenyl)sulfonyl]{3-[1-methyl-4-(pyridin-4-yl)-1H-pyrazol-3-yl]-2,4-difluorophenyl}carbamate,
ethyl [(2,5-difluorophenyl)sulfonyl]{3-[1-methyl-4-(pyridin-4-yl)-1H-pyrazol-3-yl]-2,4-difluorophenyl}carbamate,
propyl [(2,5-difluorophenyl)sulfonyl]{3-[1-methyl-4-(pyridin-4-yl)-1H-pyrazol-3-yl]-2,4-difluorophenyl}carbamate,
propan-2-yl [(2,5-difluorophenyl)sulfonyl]{3-[1-methyl-4-(pyridin-4-yl)-1H-pyrazol-3-yl]-2,4-difluorophenyl}carbamate,
N-[(2,5-difluorophenyl)sulfonyl]-N-{3-[1-methyl-4-(pyridin-4-yl)-1H-pyrazol-3-yl]-2,4-difluorophenyl}acetamide,
N-[(2,5-difluorophenyl)sulfonyl]-N-{3-[1-methyl-4-(pyridin-4-yl)-1H-pyrazol-3-yl]-2,4-difluorophenyl}-N2,N2-dimethylglycinamide,
([(2,5-difluorophenyl)sulfonyl]{3-[1-methyl-4-(pyridin-4-yl)-1H-pyrazol-3-yl]-2,4-difluorophenyl}amino)methyl acetate,
([(2,5-difluorophenyl)sulfonyl]{3-[1-methyl-4-(pyridin-4-yl)-1H-pyrazol-3-yl]-2,4-difluorophenyl}amino)methyl benzoate,
([(2,5-difluorophenyl)sulfonyl]{3-[1-methyl-4-(pyridin-4-yl)-1H-pyrazol-3-yl]-2,4-difluorophenyl}amino)methyl N,N-dimethylglycinate,
ethyl N-{[([(2,5-difluorophenyl)sulfonyl]{3-[1-methyl-4-(pyridin-4-yl)-1H-pyrazol-3-yl]-2,4-difluorophenyl}amino)methoxy]carbonyl}-N-methylglycinate,
methyl {3-[1-ethyl-4-(pyridin-4-yl)-1H-pyrazol-3-yl]-2,4-difluorophenyl}[(3-fluorophenyl)sulfonyl]carbamate,
ethyl {3-[1-ethyl-4-(pyridin-4-yl)-1H-pyrazol-3-yl]-2,4-difluorophenyl}[(3-fluorophenyl)sulfonyl]carbamate,
propyl {3-[1-ethyl-4-(pyridin-4-yl)-1H-pyrazol-3-yl]-2,4-difluorophenyl}[(3-fluorophenyl)sulfonyl]carbamate,
propan-2-yl {3-[1-ethyl-4-(pyridin-4-yl)-1H-pyrazol-3-yl]-2,4-difluorophenyl}[(3-fluorophenyl)sulfonyl]carbamate,
N-{3-[1-ethyl-4-(pyridin-4-yl)-1H-pyrazol-3-yl]-2,4-difluorophenyl}-N-[(3-fluorophenyl)sulfonyl]acetamide,
N-{3-[1-ethyl-4-(pyridin-4-yl)-1H-pyrazol-3-yl]-2,4-difluorophenyl}-N-[(3-fluorophenyl)sulfonyl]-N2,N2-dimethylglycinamide,
({3-[1-ethyl-4-(pyridin-4-yl)-1H-pyrazol-3-yl]-2,4-difluorophenyl}[(3-fluorophenyl)sulfonyl]amino)methyl acetate,
({3-[1-ethyl-4-(pyridin-4-yl)-1H-pyrazol-3-yl]-2,4-difluorophenyl}[(3-fluorophenyl)sulfonyl]amino)methyl benzoate,
({3-[1-ethyl-4-(pyridin-4-yl)-1H-pyrazol-3-yl]-2,4-difluorophenyl}[(3-fluorophenyl)sulfonyl]amino)methyl N,N-dimethylglycinate,
ethyl N-{[({3-[1-ethyl-4-(pyridin-4-yl)-1H-pyrazol-3-yl]-2,4-difluorophenyl}[(3-fluorophenyl)sulfonyl]amino)methoxy]carbonyl}-N-methylglycinate,
methyl {3-[1-ethyl-4-(pyridin-4-yl)-1H-pyrazol-3-yl]-2,4-difluorophenyl}[(2-fluorophenyl)sulfonyl]carbamate,
ethyl {3-[1-ethyl-4-(pyridin-4-yl)-1H-pyrazol-3-yl]-2,4-difluorophenyl}[(2-fluorophenyl)sulfonyl]carbamate,
propyl {3-[1-ethyl-4-(pyridin-4-yl)-1H-pyrazol-3-yl]-2,4-difluorophenyl}[(2-fluorophenyl)sulfonyl]carbamate,
propan-2-yl {3-[1-ethyl-4-(pyridin-4-yl)-1H-pyrazol-3-yl]-2,4-difluorophenyl}[(2-fluorophenyl)sulfonyl]carbamate,
N-{3-[1-ethyl-4-(pyridin-4-yl)-1H-pyrazol-3-yl]-2,4-difluorophenyl}-N-[(2-fluorophenyl)sulfonyl]acetamide,
N-{3-[1-ethyl-4-(pyridin-4-yl)-1H-pyrazol-3-yl]-2,4-difluorophenyl}-N-[(2-fluorophenyl)sulfonyl]-N2,N2-dimethylglycinamide,
({3-[1-ethyl-4-(pyridin-4-yl)-1H-pyrazol-3-yl]-2,4-difluorophenyl}[(2-fluorophenyl)sulfonyl]amino)methyl acetate,
({3-[1-ethyl-4-(pyridin-4-yl)-1H-pyrazol-3-yl]-2,4-difluorophenyl}[(2-fluorophenyl)sulfonyl]amino)methyl benzoate,
({3-[1-ethyl-4-(pyridin-4-yl)-1H-pyrazol-3-yl]-2,4-difluorophenyl}[(2-fluorophenyl)sulfonyl]amino)methyl N,N-dimethylglycinate,
ethyl N-{[({3-[1-ethyl-4-(pyridin-4-yl)-1H-pyrazol-3-yl]-2,4-difluorophenyl}[(2-fluorophenyl)sulfonyl]amino) methoxy]carbonyl)-N-methylglycinate,
methyl {3-[4-(2-aminopyridin-4-yl)-1-ethyl-1H-pyrazol-3-yl]-2,4-difluorophenyl}[(2,5-difluorophenyl)sulfonyl]carbamate,
ethyl {3-[4-(2-aminopyridin-4-yl)-1-ethyl-1H-pyrazol-3-yl]-2,4-difluorophenyl}[(2,5-difluorophenyl)sulfonyl]carbamate,
propyl {3-[4-(2-aminopyridin-4-yl)-1-ethyl-1H-pyrazol-3-yl]-2,4-difluorophenyl}[(2,5-difluorophenyl)sulfonyl]carbamate,
propan-2-yl {3-[4-(2-aminopyridin-4-yl)-1-ethyl-1H-pyrazol-3-yl]-2,4-difluorophenyl}[(2,5-difluorophenyl)sulfonyl]carbamate,
N-{3-[4-(2-aminopyridin-4-yl)-1-ethyl-1H-pyrazol-3-yl]-2,4-difluorophenyl}-N-[(2,5-difluorophenyl)sulfonyl]acetamide,
N-{3-[4-(2-aminopyridin-4-yl)-1-ethyl-1H-pyrazol-3-yl]-2,4-difluorophenyl}-N-[(2,5-difluorophenyl)sulfonyl]-N2,N2-dimethylglycinamide, ({3-[4-(2-aminopyridin-4-yl)-1-ethyl-1H-pyrazol-3-yl]-2,4-difluorophenyl}[(2,5-difluorophenyl)sulfonyl]amino) methyl acetate,
({3-[4-(2-aminopyridin-4-yl)-1-ethyl-1H-pyrazol-3-yl]-2,4-difluorophenyl}[(2,5-difluorophenyl)sulfonyl]amino)methyl benzoate,
({3-[4-(2-aminopyridin-4-yl)-1-ethyl-1H-pyrazol-3-yl]-2,4-difluorophenyl}[(2,5-difluorophenyl)sulfonyl]amino)methyl N,N-dimethylglycinate,
ethyl N-{[({3-[4-(2-aminopyridin-4-yl)-1-ethyl-1H-pyrazol-3-yl]-2,4-difluorophenyl}[(2,5-difluorophenyl)sulfonyl]amino)methoxy]carbonyl}-N-methylglycinate,
methyl [(2,5-difluorophenyl)sulfonyl]{3-[1-ethyl-4-(pyridin-4-yl)-1H-pyrazol-3-yl]-4-fluorophenyl}carbamate,
ethyl [(2,5-difluorophenyl)sulfonyl]{3-[1-ethyl-4-(pyridin-4-yl)-1H-pyrazol-3-yl]-4-fluorophenyl}carbamate,
propyl [(2,5-difluorophenyl)sulfonyl]{3-[1-ethyl-4-(pyridin-4-yl)-1H-pyrazol-3-yl]-4-fluorophenyl}carbamate,
propan-2-yl [(2,5-difluorophenyl)sulfonyl]{3-[1-ethyl-4-(pyridin-4-yl)-1H-pyrazol-3-yl]-4-fluorophenyl}carbamate,
N-[(2,5-difluorophenyl)sulfonyl]-N-{3-[1-ethyl-4-(pyridin-4-yl)-1H-pyrazol-3-yl]-4-fluorophenyl}acetamide,
N-[(2,5-difluorophenyl)sulfonyl]-N-{3-[1-ethyl-4-(pyridin-4-yl)-1H-pyrazol-3-yl]-4-fluorophenyl}-N2,N2-dimethylglycinamide,
([(2,5-difluorophenyl)sulfonyl]{3-[1-ethyl-4-(pyridin-4-yl)-1H-pyrazol-3-yl]-4-fluorophenyl}amino)methyl acetate,
([(2,5-difluorophenyl)sulfonyl]{3-[1-ethyl-4-(pyridin-4-yl)-1H-pyrazol-3-yl]-4-fluorophenyl}amino)methyl benzoate,
([(2,5-difluorophenyl)sulfonyl]{3-[1-ethyl-4-(pyridin-4-yl)-1H-pyrazol-3-yl]-4-fluorophenyl}amino)methyl N,N-dimethylglycinate,
ethyl N-{[([(2,5-difluorophenyl)sulfonyl]{3-[1-ethyl-4-(pyridin-4-yl)-1H-pyrazol-3-yl]-4-fluorophenyl}amino)methoxy]carbonyl}-N-methylglycinate,
methyl [(2,5-difluorophenyl)sulfonyl]{3-[1-ethyl-4-(pyridin-4-yl)-1H-pyrazol-3-yl]-2-fluorophenyl}carbamate,
ethyl [(2,5-difluorophenyl)sulfonyl]{3-[1-ethyl-4-(pyridin-4-yl)-1H-pyrazol-3-yl]-2-fluorophenyl}carbamate,
propyl [(2,5-difluorophenyl)sulfonyl]{3-[1-ethyl-4-(pyridin-4-yl)-1H-pyrazol-3-yl]-2-fluorophenyl}carbamate,
propan-2-yl [(2,5-difluorophenyl)sulfonyl]{3-[1-ethyl-4-(pyridin-4-yl)-1H-pyrazol-3-yl]-2-fluorophenyl}carbamate,
N-[(2,5-difluorophenyl)sulfonyl]-N-{3-[1-ethyl-4-(pyridin-4-yl)-1H-pyrazol-3-yl]-2-fluorophenyl}acetamide,
N-[(2,5-difluorophenyl)sulfonyl]-N-{3-[1-ethyl-4-(pyridin-4-yl)-1H-pyrazol-3-yl]-2-fluorophenyl}-N2,N2-dimethylglycinamide,
([(2,5-difluorophenyl)sulfonyl]{3-[1-ethyl-4-(pyridin-4-yl)-1H-pyrazol-3-yl]-2-fluorophenyl}amino)methyl acetate,
([(2,5-difluorophenyl)sulfonyl]{3-[1-ethyl-4-(pyridin-4-yl)-1H-pyrazol-3-yl]-2-fluorophenyl}amino)methyl benzoate,
([(2,5-difluorophenyl)sulfonyl]{3-[1-ethyl-4-(pyridin-4-yl)-1H-pyrazol-3-yl]-2-fluorophenyl}amino)methyl N,N-dimethylglycinate,
ethyl N-{[([(2,5-difluorophenyl)sulfonyl]{3-[1-ethyl-4-(pyridin-4-yl)-1H-pyrazol-3-yl]-2-fluorophenyl}amino) methoxy]carbonyl}-N-methylglycinate,
methyl [(2,5-difluorophenyl)sulfonyl]{3-[1-ethyl-4-(pyridin-4-yl)-1H-pyrazol-3-yl]-2-methylphenyl}carbamate,
ethyl [(2,5-difluorophenyl)sulfonyl]{3-[1-ethyl-4-(pyridin-4-yl)-1H-pyrazol-3-yl]-2-methylphenyl}carbamate,
propyl [(2,5-difluorophenyl)sulfonyl]{3-[1-ethyl-4-(pyridin-4-yl)-1H-pyrazol-3-yl]-2-methylphenyl}carbamate,
propan-2-yl [(2,5-difluorophenyl)sulfonyl]{3-[1-ethyl-4-(pyridin-4-yl)-1H-pyrazol-3-yl]-2-methylphenyl}carbamate,
N-[(2,5-difluorophenyl)sulfonyl]-N-{3-[1-ethyl-4-(pyridin-4-yl)-1H-pyrazol-3-yl]-2-methylphenyl}acetamide,
N-[(2,5-difluorophenyl)sulfonyl]-N-{3-[1-ethyl-4-(pyridin-4-yl)-1H-pyrazol-3-yl]-2-methylphenyl}-N2,N2-dimethylglycinamide,
([(2,5-difluorophenyl)sulfonyl]{3-[1-ethyl-4-(pyridin-4-yl)-1H-pyrazol-3-yl]-2-methylphenyl}amino) methyl acetate,
([(2,5-difluorophenyl)sulfonyl]{3-[1-ethyl-4-(pyridin-4-yl)-1H-pyrazol-3-yl]-2-methylphenyl}amino) methyl benzoate,
([(2,5-difluorophenyl)sulfonyl]{3-[1-ethyl-4-(pyridin-4-yl)-1H-pyrazol-3-yl]-2-methylphenyl}amino) methyl N,N-dimethylglycinate,
ethyl N-{[([(2,5-difluorophenyl)sulfonyl]{3-[1-ethyl-4-(pyridin-4-yl)-1H-pyrazol-3-yl]-2-methylphenyl}amino) methoxy]carbonyl}-N-methylglycinate,
methyl {3-[4-(2-aminopyrimidin-4-yl)-1-ethyl-1H-pyrazol-3-yl]-2,4-difluorophenyl}[(2,5-difluorophenyl)sulfonyl]carbamate,
ethyl {3-[4-(2-aminopyrimidin-4-yl)-1-ethyl-1H-pyrazol-3-yl]-2,4-difluorophenyl}[(2,5-difluorophenyl)sulfonyl]carbamate,
propyl {3-[4-(2-aminopyrimidin-4-yl)-1-ethyl-1H-pyrazol-3-yl]-2,4-difluorophenyl}[(2,5-difluorophenyl)sulfonyl]carbamate,
propan-2-yl {3-[4-(2-aminopyrimidin-4-yl)-1-ethyl-1H-pyrazol-3-yl]-2,4-difluorophenyl}[(2,5-difluorophenyl)sulfonyl]carbamate,
N-{3-[4-(2-aminopyrimidin-4-yl)-1-ethyl-1H-pyrazol-3-yl]-2,4-difluorophenyl}-N-[(2,5-difluorophenyl)sulfonyl]acetamide,
N-{3-[4-(2-aminopyrimidin-4-yl)-1-ethyl-1H-pyrazol-3-yl]-2,4-difluorophenyl}-N-[(2,5-difluorophenyl)sulfonyl]-N2,N2-dimethylglycinamide,
({3-[4-(2-aminopyrimidin-4-yl)-1-ethyl-1H-pyrazol-3-yl]-2,4-difluorophenyl}[(2,5-difluorophenyl)sulfonyl]amino)methyl acetate,
({3-[4-(2-aminopyrimidin-4-yl)-1-ethyl-1H-pyrazol-3-yl]-2,4-difluorophenyl}[(2,5-difluorophenyl)sulfonyl]amino)methyl benzoate,
({3-[4-(2-aminopyrimidin-4-yl)-1-ethyl-1H-pyrazol-3-yl]-2,4-difluorophenyl}[(2,5-difluorophenyl)sulfonyl]amino)methyl N,N-dimethylglycinate,
ethyl N-{[({3-[4-(2-aminopyrimidin-4-yl)-1-ethyl-1H-pyrazol-3-yl]-2,4-difluorophenyl}[(2,5-difluorophenyl)sulfonyl]amino)methoxy]carbonyl}-N-methylglycinate,
methyl {3-[4-(2-aminopyrimidin-4-yl)-1-ethyl-1H-pyrazol-3-yl]-2-fluorophenyl}[(2,5-difluorophenyl)sulfonyl]carbamate, ethyl {3-[4-(2-aminopyrimidin-4-yl)-1-ethyl-1H-pyrazol-3-yl]-2-fluorophenyl}[(2,5-difluorophenyl)sulfonyl]carbamate, propyl {3-[4-(2-aminopyrimidin-4-yl)-1-ethyl-1H-pyrazol-3-yl]-2-fluorophenyl}[(2,5-difluorophenyl)sulfonyl]carbamate, propan-2-yl {3-[4-(2-aminopyrimidin-4-yl)-1-ethyl-1H-pyrazol-3-yl]-2-fluorophenyl}[(2,5-difluorophenyl)sulfonyl]carbamate, N-{3-[4-(2-aminopyrimidin-4-yl)-1-ethyl-1H-pyrazol-3-yl]-2-fluorophenyl}-N-[(2,5-difluorophenyl)sulfonyl]acetamide, N-{3-[4-(2-aminopyrimidin-4-yl)-1-ethyl-1H-pyrazol-3-yl]-2-fluorophenyl}-N-[(2,5-difluorophenyl)sulfonyl]-N2,N2-dimethylglycinamide, ({3-[4-(2-aminopyrimidin-4-yl)-1-ethyl-1H-pyrazol-3-yl]-2-fluorophenyl}[(2,5-difluorophenyl)sulfonyl]amino)methyl acetate, ({3-[4-(2-aminopyrimidin-4-yl)-1-ethyl-1H-pyrazol-3-yl]-2-fluorophenyl}[(2,5-difluorophenyl)sulfonyl]amino)methyl benzoate, ({3-[4-(2-aminopyrimidin-4-yl)-1-ethyl-1H-pyrazol-3-yl]-2-fluorophenyl}[(2,5-difluorophenyl)sulfonyl]amino)methyl N,N-dimethylglycinate, ethyl N-{[({3-[4-(2-aminopyrimidin-4-yl)-1-ethyl-1H-pyrazol-3-yl]-2-fluorophenyl}[(2,5-difluorophenyl)sulfonyl]amino)methoxy]carbonyl}-N-methylglycinate, methyl {2,4-difluoro-3-[1-(2-fluoroethyl)-4-(pyridin-4-yl)-1H-pyrazol-3-yl]phenyl}[(2,5-difluorophenyl)sulfonyl]carbamate, ethyl {2,4-difluoro-3-[1-(2-fluoroethyl)-4-(pyridin-4-yl)-1H-pyrazol-3-yl]phenyl}[(2,5-difluorophenyl)sulfonyl]carbamate, propyl {2,4-difluoro-3-[1-(2-fluoroethyl)-4-(pyridin-4-yl)-1H-pyrazol-3-yl]phenyl}[(2,5-difluorophenyl)sulfonyl]carbamate, propan-2-yl {2,4-difluoro-3-[1-(2-fluoroethyl)-4-(pyridin-4-yl)-1H-pyrazol-3-yl]phenyl}[(2,5-difluorophenyl)sulfonyl]carbamate, N-{2,4-difluoro-3-[1-(2-fluoroethyl)-4-(pyridin-4-yl)-1H-pyrazol-3-yl]phenyl}-N-[(2,5-difluorophenyl) sulfonyl]acetamide, N-{2,4-difluoro-3-[1-(2-fluoroethyl)-4-(pyridin-4-yl)-1H-pyrazol-3-yl]phenyl}-N-[(2,5-difluorophenyl) sulfonyl]-N2,N2-dimethylglycinamide, ({2,4-difluoro-3-[1-(2-fluoroethyl)-4-(pyridin-4-yl)-1H-pyrazol-3-yl]phenyl}[(2,5-difluorophenyl) sulfonyl]amino)methyl acetate, ({2,4-difluoro-3-[1-(2-fluoroethyl)-4-(pyridin-4-yl)-1H-pyrazol-3-yl]phenyl}[(2,5-difluorophenyl) sulfonyl]amino)methyl benzoate, ({2,4-difluoro-3-[1-(2-fluoroethyl)-4-(pyridin-4-yl)-1H-pyrazol-3-yl]phenyl}[(2,5-difluorophenyl) sulfonyl]amino)methyl N,N-dimethylglycinate, ethyl N-{[({2,4-difluoro-3-[1-(2-fluoroethyl)-4-(pyridin-4-yl)-1H-pyrazol-3-yl]phenyl}[(2,5-difluorophenyl)sulfonyl]amino)methoxy]carbonyl}-N-methylglycinate, methyl {3-[4-(2-aminopyrimidin-4-yl)-1-(2-fluoroethyl)-1H-pyrazol-3-yl]-2,4-difluorophenyl}[(2,5-difluorophenyl) sulfonyl]carbamate, ethyl (3-[4-(2-aminopyrimidin-4-yl)-1-(2-fluoroethyl)-1H-pyrazol-3-yl]-2,4-difluorophenyl)[(2,5-difluorophenyl) sulfonyl]carbamate, propyl {3-[4-(2-aminopyrimidin-4-yl)-1-(2-fluoroethyl)-1H-pyrazol-3-yl]-2,4-difluorophenyl}[(2,5-difluorophenyl),sulfonyl]carbamate, propan-2-yl {3-[4-(2-aminopyrimidin-4-yl)-1-(2-fluoroethyl)-1H-pyrazol-3-yl]-2,4-difluorophenyl}[(2,5-difluorophenyl)sulfonyl]carbamate, N-{3-[4-(2-aminopyrimidin-4-yl)-1-(2-fluoroethyl)-1H-pyrazol-3-yl]-2,4-difluorophenyl}-N-[(2,5-difluorophenyl)sulfonyl]acetamide, N-{3-[4-(2-aminopyrimidin-4-yl)-1-(2-fluoroethyl)-1H-pyrazol-3-yl]-2,4-difluorophenyl}-N-[(2,5-difluorophenyl)sulfonyl]-N2,N2-dimethylglycinamide, ({3-[4-(2-aminopyrimidin-4-yl)-1-(2-fluoroethyl)-1H-pyrazol-3-yl]-2,4-difluorophenyl}[(2,5-difluorophenyl)sulfonyl]amino)methyl acetate, ({3-[4-(2-aminopyrimidin-4-yl)-1-(2-fluoroethyl)-1H-pyrazol-3-yl]-2,4-difluorophenyl}[(2,5-difluorophenyl)sulfonyl]amino)methyl benzoate, ({3-[4-(2-aminopyrimidin-4-yl)-1-(2-fluoroethyl)-1H-pyrazol-3-yl]-2,4-difluorophenyl}[(2,5-difluorophenyl)sulfonyl]amino)methyl N,N-dimethylglycinate, ethyl N-{[({3-[4-(2-aminopyrimidin-4-yl)-1-(2-fluoroethyl)-1H-pyrazol-3-yl]-2,4-difluorophenyl}[(2,5-fluorophenyl)sulfonyl]amino)methoxy]carbonyl}-N-methylglycinate, methyl [(2,5-difluorophenyl)sulfonyl](2,4-difluoro-3-{1-[2-(piperidin-1-yl)ethyl]-4-(pyridin-4-yl)-1H-pyrazol-3-yl}phenyl)carbamate, ethyl [(2,5-difluorophenyl)sulfonyl](2,4-difluoro-3-{1-[2-(piperidin-1-yl)ethyl]-4-(pyridin-4-yl)-1H-pyrazol-3-yl}phenyl)carbamate, propyl [(2,5-difluorophenyl)sulfonyl](2,4-difluoro-3-{1-[2-(piperidin-1-yl)ethyl]-4-(pyridin-4-yl)-1H-pyrazol-3-yl}phenyl)carbamate, propan-2-yl [(2,5-difluorophenyl)sulfonyl](2,4-difluoro-3-{1-[2-(piperidin-1-yl)ethyl]-4-(pyridin-4-yl)-1H-pyrazol-3-yl}phenyl)carbamate, N-[(2,5-difluorophenyl)sulfonyl]-N-(2,4-difluoro-3-{1-[2-(piperidin-1-yl)ethyl]-4-(pyridin-4-yl)-1H-pyrazol-3-yl}phenyl)acetamide, N-[(2,5-difluorophenyl)sulfonyl]-N-(2,4-difluoro-3-{1-[2-(piperidin-1-yl)ethyl]-4-(pyridin-4-yl)-1H-pyrazol-3-yl}phenyl)-N2,N2-dimethylglycinamide, {[(2,5-difluorophenyl)sulfonyl](2,4-difluoro-3-{1-[2-(piperidin-1-yl)ethyl]-4-(pyridin-4-yl)-1H-pyrazol-3-yl}phenyl)amino}methyl acetate, {[(2,5-difluorophenyl)sulfonyl](2,4-difluoro-3-{1-[2-(piperidin-1-yl)ethyl]-4-(pyridin-4-yl)-1H-pyrazol-3-yl}phenyl)amino}methyl benzoate, {[(2,5-difluorophenyl)sulfonyl](2,4-difluoro-3-{1-[2-(piperidin-1-yl)ethyl]-4-(pyridin-4-yl)-1H-pyrazol-3-yl}phenyl)amino}methyl N,N-dimethylglycinate and ethyl N-[({[(2,5-difluorophenyl)sulfonyl](2,4-difluoro-3-{1-[2-(piperidin-1-yl)ethyl]-4-(pyridin-4-yl)-1H-pyrazol-3-yl}phenyl)amino}methoxy)carbonyl]-N-methylglycinate.

9. A process for preparing a compound of formula (I) as defined in claim 1 characterized in that the process comprises:

a) reacting an optionally protected sulfonamido 3,4-diarylpyrazole compound of formula (II):

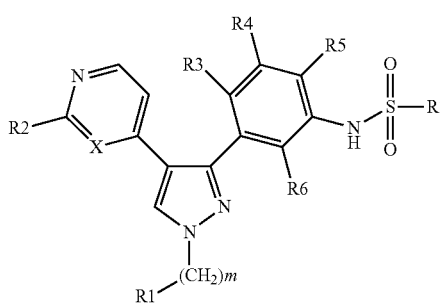

wherein R1, R2, R3, R4, R5, R6, R7, X and m are as defined in claim 1, with any suitable agent for inserting on the sulfonamide nitrogen atom the desired R8 group, wherein R8 is as defined in claim 1, according to any one of the alternative steps:

a1) with an acyl compound of formula (III):

wherein W is a suitable leaving group such as hydroxy, halogen or a group OCOR27', wherein R27' is hydrogen or a group optionally substituted selected from straight or branched $(C_1-C_8)$ alkyl, $(C_2-C_8)$ alkenyl, $(C_2-C_8)$ alkynyl, $(C_3-C_8)$ cycloalkyl, $(C_3-C_8)$ cycloalkenyl, heterocyclyl, aryl and heteroaryl, to give a compound of formula (I) wherein R8 is COR27, wherein R27 is R27' and R27' is as defined above;

or a2) with a halogenoformate compound of formula (IV):

wherein Hal is halogen and R30 is as defined in claim 1, to give a compound of formula (I) wherein R8 is COR27, wherein R27 is OR30 and R30 is as defined above;

or a3) with an alpha-haloalkyl compound of formula (V):

wherein Hal is halogen and R28 and R29 are as defined in claim 1, to give a compound of formula (I) wherein R8 is CHR28OCOR29, wherein R28 and R29 are as defined above, followed by optional removal of the protecting group, if present;

b) if necessary converting the resultant compound of formula (I):

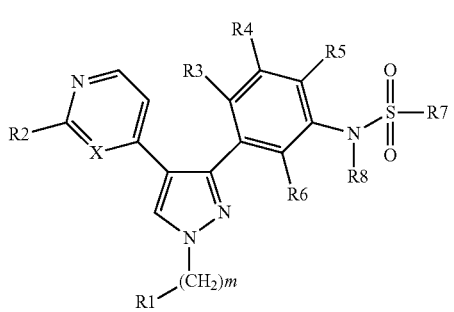

wherein R1, R2, R3, R4, R5, R6, R7, R8, X and m are as defined in claim 1, into another compound of formula (I) wherein one or more of R1, R2, R3, R4, R5, R6, R7, X and m is different by known reactions; and/or separating the resultant compound of formula (I) into the single isomers; and/or converting a compound of formula (I) as defined above into a pharmaceutically acceptable salt or converting the salt thereof into the free compound of formula (I) as defined above.

10. A method for treating a disease selected from the group consisting of cancer and cell proliferative disorders comprising administering to a mammal in need thereof an effective amount of a compound of claim 1.

11. The method according to claim 10 wherein the cancer is selected from the group consisting of carcinoma; hematopoietic tumors of lymphoid lineage; hematopoietic tumors of myeloid lineage; tumors of mesenchymal origin; tumors of the central and peripheral nervous system; melanoma; seminoma; teratocarcinoma; osteosarcoma; xeroderma pigmentosum; keratoxanthoma; thyroid follicular cancer; and Kaposi's sarcoma.

12. The method according to claim 10 wherein the cell proliferative disorder is selected from the group consisting of benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

13. The method according to claim 10 further comprising subjecting the mammal in need thereof to a radiation therapy or chemotherapy regimen in combination with at least one cytostatic or cytotoxic agent.

14. The method according to claim 10 wherein the mammal in need thereof is a human.

15. A method for inhibiting tumor angiogenesis and metastasis comprising administering to a mammal in need thereof an effective amount of a compound of claim 1.

16. An in vitro method for inhibiting the RAF family activity which comprises contacting the said receptor with an effective amount of a compound of formula (I) as defined in claim 1.

17. A pharmaceutical composition comprising a therapeutically effective amount of a compound of formula (I) or a pharmaceutically acceptable salt thereof, as defined in claim 1, and at least one pharmaceutically acceptable excipient, carrier and/or diluent.

18. A pharmaceutical composition according to claim 17 further comprising one or more chemotherapeutic agents.

19. A product or kit comprising a compound of formula (I) or a pharmaceutically acceptable salt thereof, as defined in claim 1, or pharmaceutical compositions thereof as defined in claim 17 and one or more chemotherapeutic agents, as a combined preparation for simultaneous, separate or sequential use in anticancer therapy.

20. A compound of claim 6, or a pharmaceutically acceptable salt thereof, wherein R2 is hydrogen.

21. A compound of claim 7, or a pharmaceutically acceptable salt thereof, wherein R2 is hydrogen.

22. The method according to claim 11, wherein:
the carcinoma is carcinoma of the bladder, breast, colon, kidney, liver, lung, including small cell lung cancer, esophagus, gall-bladder, ovary, pancreas, stomach, cervix, thyroid, prostate, skin, or squamous cell;
the hematopoietic tumors of lymphoid lineage are leukemia, acute lymphocytic leukemia, acute lymphoblastic leukemia, B-cell lymphoma, T-cell-lymphoma, Hodgkin's lymphoma, non-Hodgkin's lymphoma, hairy cell lymphoma or Burkett's lymphoma;

the hematopoietic tumors of myeloid lineage are acute myelogenous leukemia, chronic myelogenous leukemia, myelodysplastic syndrome or promyelocytic leukemia;
the tumors of mesenchymal origin are fibrosarcoma or rhabdomyosarcoma; and
the tumors of the central and peripheral nervous system are astrocytoma neuroblastoma, glioma or schwannomas.

* * * * *